(12) United States Patent
Treder et al.

(10) Patent No.: US 11,167,029 B2
(45) Date of Patent: Nov. 9, 2021

(54) COMBINATION OF A CD30XCD16 ANTIBODY WITH A PD-1 ANTAGONIST FOR THERAPY

(71) Applicant: Affimed GmbH, Heidelberg (DE)

(72) Inventors: Martin Treder, Heidelberg (DE); Uwe Reusch, Maikammer (DE); Jens-Peter Marschner, Seeheim-Jugenheim (DE); Stefan Knackmuss, Plankstadt (DE)

(73) Assignee: AFFIMED GMBH, Heidelberg (DE)

( * ) Notice: Subject to any disclaimer, the term of this patent is extended or adjusted under 35 U.S.C. 154(b) by 0 days.

(21) Appl. No.: 15/788,177

(22) Filed: Oct. 19, 2017

(65) Prior Publication Data

US 2018/0085456 A1 Mar. 29, 2018

Related U.S. Application Data

(63) Continuation-in-part of application No. PCT/EP2016/060113, filed on May 4, 2016.

(30) Foreign Application Priority Data

| | | |
|---|---|---|
| May 4, 2015 | (EP) | 15166303 |
| Jan. 25, 2016 | (EP) | 16152650 |

(51) Int. Cl.
| | |
|---|---|
| *A61K 39/395* | (2006.01) |
| *C07K 16/28* | (2006.01) |
| *C07K 16/30* | (2006.01) |
| *A61K 39/00* | (2006.01) |

(52) U.S. Cl.
CPC .... *A61K 39/39558* (2013.01); *A61K 39/3955* (2013.01); *C07K 16/283* (2013.01); *C07K 16/2818* (2013.01); *C07K 16/2878* (2013.01); *C07K 16/3061* (2013.01); *A61K 2039/507* (2013.01); *C07K 2317/31* (2013.01); *C07K 2317/565* (2013.01); *C07K 2317/626* (2013.01); *C07K 2317/76* (2013.01); *C07K 2317/92* (2013.01)

(58) Field of Classification Search
CPC .............. C07K 16/2818; C07K 16/283; C07K 16/2878
See application file for complete search history.

(56) References Cited

U.S. PATENT DOCUMENTS

| | | |
|---|---|---|
| 2014/0099254 A1 | 4/2014 | Chang et al. |
| 2014/0178370 A1 | 6/2014 | Freeman et al. |
| 2017/0247455 A1* | 8/2017 | Jure-Kunkel ...... C07K 16/2818 |

FOREIGN PATENT DOCUMENTS

WO 2006/125668 A2 11/2006

OTHER PUBLICATIONS

Ansell et al. (The New England J. Med. Dec. 6, 2014, 372 (4): 311-319) (Year: 2014).*
Rothe et al. (Blood Apr. 17, 2015, 125(26): 4024-4031) (Year: 2015).*
Bashey et al. (Blood Feb. 12, 2009, 113 (7): 1581-1588) (Year: 2009).*
Zhao et al. (Blood, (Dec. 3, 2015) vol. 126, No. 23, p. 2747. Meeting Info: 57th Annual Meeting of the American Society of Hematology, ASH 2015) (Year: 2015).*
Marschner et al. (Oncology Research and Treatment, (Feb. 24, 2016) vol. 39,Supp. Suppl. 1, p. 28. Abstract No. ID 0050, Meeting Info: 32, Deutscher Krebskongress, DKK 2016, Berlin, Germany. Feb. 24, 2016-Feb. 27, 2016) (Year: 2016).*
Zhao et al. (European Journal of Cancer, (Mar. 2016) vol. 55, No. Suppl. 1, p. S20 Meeting Info. 3rd Immunotherapy of Cancer Conference Munich, Germany. Mar. 2-23, 2016) (Year: 2016).*
Zhao et al. (Cancer Research, (2016) vol. 76, No. 14, Supp. Supplement. Abstract No. 2323, Meeting Info: 107th Annual Meeting of the American Association for Cancer Research, AACR 2016. New Orleans, LA, United States. Apr. 16, 2016-Apr. 20, 2016 ) (Year: 2016).*
Zhao et al. (Journal of Clinical Oncology, (May 20, 2015) vol. 33, No. 15, Supp. Suppl. 1. Abstract No. 3050. Meeting Info: 2015 Annual Meeting of the American Society of Clinical Oncology, ASCO. Chicago) (Year: 2015).*
International Search Report and Written Opinion of the International Searching Authority dated Jun. 30, 2016, which issued during prosecution of International Application No. PCT/EP2016/060113.
Anonymous. "For Immediate Release: Affimed ASCO Data Demonstrate Consistent Potency of NK-Cell-Engaging Combination Therapy with Checkpoint Modulators" May 29, 2015, retrieved from http://www.affimed.com/pdf/20150529_affimed_asco_poster_afm13_final.pdf.
Dolan, et al. "PD-1 Pathway Inhibitors: Changing the Landscape of Cancer Immunotherapy" Cancer Control, Jul. 2014, 21(3):231-237.
Reusch, et al. "A Novel Tetravalent Bispecific TandAb (CD30/CD16A) efficiently recruits NK cells for the lysis of CD30+ tumor cells" mAbs, May/Jun. 2014, 6(3):728-739.
Michael R. Green, et al., Integrative Analysis Reveals Selective 9p24.1 Amplification, Increased PD-1 Ligand Expression, and Further Induction Via JAK2 in Nodular Sclerosing Hodgkin Lymphoma and Primary Mediastinal Large B-Cell Lymphoma, Blood (2010) 116(17):3268-3277.
Katrin S. Reiners, et al., Rescue of Impaired NK Cell Activity in Hodgkin Lymphoma With Bispecific Antibodies In Vitro and in Patients, Molecular Therapy (Apr. 2018) vol. 21, No. 4, 895-903.
Jacalyn Rosenblatt, et al., PD-1 Blockade by CT-011, Anti PD-1 Antibody, Enhances Ex-Vivo T Cell Responses to Autologous Dendritic/Myeloma Fusion Vaccine, J. Immunother. (Jun. 2011) 34(5):409-418.
Maulik Vyas, et al., Natural Ligands and Antibody-Based Fusion Proteins: Harnessing the Immune System Against Cancer, Trends in Molecular Medicine (2014) vol. 20, No. 2, p. 72-80.

(Continued)

*Primary Examiner* — Peter J Reddig
(74) *Attorney, Agent, or Firm* — Duane Morris LLP; Thomas J. Kowalski; Deborah L. Lu

(57) ABSTRACT

Described is a combination therapy of (i) a multifunctional antibody having specificity for CD30 and CD16A and (ii) an anti-PD-1 antibody for the treatment of a tumor, in particular Hodgkin lymphoma.

17 Claims, 14 Drawing Sheets

Specification includes a Sequence Listing.

(56) References Cited

OTHER PUBLICATIONS

Petro Fessas et al., A molecular and preclinical comparison of the PD-1-targeted T-cell checkpoint inhibitors nivolumab and pembrolizumab, Seminars in Oncology 44 (2017) 136-140.

Hyun Tae Lee et al., Molecular Interactions of Antibody Drugs Targeting PD-1, PD-L1, and CTLA-4 in Immuno-Oncology, Molecules 2019, 24, 1190.

Justin C. Moser et al., Comparative-effectiveness of pembrolizumab vs. nivolumab for patients with metastatic melanoma, Acta Oncologica 2020, 59(4):434-437.

Francesco Passiglia et al., Looking for the best immune-checkpoint inhibitor in pre-treated NSCLC pateitns: An indirect comparison between nivolumab, pembrolizumab and atezolizumab, Int. J. Cancer, 2018, 142:1277-1284.

A. Sawas et al., Clinical and Biological Evaluation of the Novel CD30/CD16A Tetravalent Bispecific Antibody (AFM13) In Relapsed or Refractory CD30-Positive Lymphoma With Cutaneous Presentation: A Biomarker Phase IB/IIA Study (NCT03192202), Hematol. Oncol., 2019, 37:314-316.

Matteo Donadon et al. Increased Infiltration of Natural Killer and T Cells in Colorectal Liver Metastases Improves Patient Overall Survival, J. Gastrointest Surg 2017, 21:1226-1236.

Iva Truxova et al, Mature dendritic cells correlate with favorable immune infiltrate and improved prognosis in ovarian carcinoma patients, J. Immuno Therapy Cancer, 2018, 6:139.

\* cited by examiner

SEQUENCE LISTING

```
<160> NUMBER OF SEQ ID NOS: 5

<210> SEQ ID NO 1
<211> LENGTH: 483
<212> TYPE: PRT
<213> ORGANISM: artificial sequence
<220> FEATURE:
<223> OTHER INFORMATION: Fv tandem diabody

<400> SEQUENCE: 1

Gln Val Gln Leu Val Gln Ser Gly Ala Glu Val Lys Lys Pro Gly Glu
1               5                   10                  15

Ser Leu Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ser Ala Tyr Tyr Tyr Asp Phe Ala Asp Tyr Trp Gly Gln
            100                 105                 110

Gly Thr Leu Val Thr Val Ser Ser Gly Gly Ser Gly Gly Ser Gly Gly
        115                 120                 125

Ser Asp Ile Val Met Thr Gln Ser Pro Lys Phe Met Ser Thr Ser Val
    130                 135                 140

Gly Asp Arg Val Thr Val Thr Cys Lys Ala Ser Gln Asn Val Gly Thr
145                 150                 155                 160

Asn Val Ala Trp Phe Gln Gln Lys Pro Gly Gln Ser Pro Lys Val Leu
                165                 170                 175

Ile Tyr Ser Ala Ser Tyr Arg Tyr Ser Gly Val Pro Asp Arg Phe Thr
            180                 185                 190

Gly Ser Gly Ser Gly Thr Asp Phe Thr Leu Thr Ile Ser Asn Val Gln
        195                 200                 205

Ser Glu Asp Leu Ala Glu Tyr Phe Cys Gln Gln Tyr His Thr Tyr Pro
    210                 215                 220
```

Leu Thr Phe Gly Gly Thr Lys Leu Glu Ile Asn Gly Gly Ser Gly
225                 230                 235                 240

Gly Ser Gly Gly Ser Gln Val Gln Leu Gln Gln Ser Gly Ala Glu Leu
            245                 250                 255

Ala Arg Pro Gly Ala Ser Val Lys Met Ser Cys Lys Ala Ser Gly Tyr
        260                 265                 270

Thr Phe Thr Thr Tyr Thr Ile His Trp Val Arg Gln Arg Pro Gly His
        275                 280                 285

Asp Leu Glu Trp Ile Gly Tyr Ile Asn Pro Ser Ser Gly Tyr Ser Asp
        290                 295                 300

Tyr Asn Gln Asn Phe Lys Gly Lys Thr Thr Leu Thr Ala Asp Lys Ser
305                 310                 315                 320

Ser Asn Thr Ala Tyr Met Gln Leu Asn Ser Leu Thr Ser Glu Asp Ser
                325                 330                 335

Ala Val Tyr Tyr Cys Ala Arg Arg Ala Asp Tyr Gly Asn Tyr Glu Tyr
            340                 345                 350

Thr Trp Phe Ala Tyr Trp Gly Gln Gly Thr Thr Val Thr Val Ser Ser
        355                 360                 365

Gly Gly Ser Gly Gly Ser Gly Ser Ser Tyr Val Leu Thr Gln Pro
    370                 375                 380

Ser Ser Val Ser Val Ala Pro Gly Gln Thr Ala Thr Ile Ser Cys Gly
385                 390                 395                 400

Gly His Asn Ile Gly Ser Lys Asn Val His Trp Tyr Gln Gln Arg Pro
                405                 410                 415

Gly Gln Ser Pro Val Leu Val Ile Tyr Gln Asp Asn Lys Arg Pro Ser
            420                 425                 430

Gly Ile Pro Glu Arg Phe Ser Gly Ser Asn Ser Gly Asn Thr Ala Thr
        435                 440                 445

Leu Thr Ile Ser Gly Thr Gln Ala Met Asp Glu Ala Asp Tyr Tyr Cys
450                 455                 460

Gln Val Trp Asp Asn Tyr Ser Val Leu Phe Gly Gly Gly Thr Lys Leu
465                 470                 475                 480

Thr Val Leu

<210> SEQ ID NO 2
<211> LENGTH: 123
<212> TYPE: PRT
<213> ORGANISM: artificial sequence
<220> FEATURE:
<223> OTHER INFORMATION: FH of anti-CD30 domain

<400> SEQUENCE: 2

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Thr Tyr
            20                  25                  30

Thr Ile His Trp Val Arg Gln Arg Pro Gly His Asp Leu Glu Trp Ile
        35                  40                  45

Gly Tyr Ile Asn Pro Ser Ser Gly Tyr Ser Asp Tyr Asn Gln Asn Phe
    50                  55                  60

Lys Gly Lys Thr Thr Leu Thr Ala Asp Lys Ser Ser Asn Thr Ala Tyr
65                  70                  75                  80

Met Gln Leu Asn Ser Leu Thr Ser Glu Asp Ser Ala Val Tyr Tyr Cys
                85                  90                  95

```
Ala Arg Arg Ala Asp Tyr Gly Asn Tyr Glu Tyr Thr Trp Phe Ala Tyr
            100                 105                 110

Trp Gly Gln Gly Thr Thr Val Thr Val Ser Ser
        115                 120

<210> SEQ ID NO 3
<211> LENGTH: 107
<212> TYPE: PRT
<213> ORGANISM: artificial sequence
<220> FEATURE:
<223> OTHER INFORMATION: VL of anti-CD30 domain

<400> SEQUENCE: 3

Asp Ile Val Met Thr Gln Ser Pro Lys Phe Met Ser Thr Ser Val Gly
1               5                   10                  15

Asp Arg Val Thr Val Thr Cys Lys Ala Ser Gln Asn Val Gly Thr Asn
            20                  25                  30

Val Ala Trp Phe Gln Gln Lys Pro Gly Gln Ser Pro Lys Val Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr His Thr Tyr Pro Leu
                85                  90                  95

Thr Phe Gly Gly Gly Thr Lys Leu Glu Ile Asn
            100                 105

<210> SEQ ID NO 4
<211> LENGTH: 120
<212> TYPE: PRT
<213> ORGANISM: artificial sequence
<220> FEATURE:
<223> OTHER INFORMATION: VH of anti-CD16A

<400> SEQUENCE: 4

Gln Val Gln Leu Val Gln Ser Gly Ala Glu Val Lys Lys Pro Gly Glu
1               5                   10                  15

Ser Leu Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ser Ala Tyr Tyr Tyr Asp Phe Ala Asp Tyr Trp Gly Gln
            100                 105                 110

Gly Thr Leu Val Thr Val Ser Ser
        115                 120

<210> SEQ ID NO 5
<211> LENGTH: 106
<212> TYPE: PRT
<213> ORGANISM: artificial sequence
<220> FEATURE:
<223> OTHER INFORMATION: VL of anti-CD16A domain
```

```
-continued

<400> SEQUENCE: 5

Ser Tyr Val Leu Thr Gln Pro Ser Ser Val Ser Val Ala Pro Gly Gln
1               5                   10                  15

Thr Ala Thr Ile Ser Cys Gly Gly His Asn Ile Gly Ser Lys Asn Val
            20                  25                  30

His Trp Tyr Gln Gln Arg Pro Gly Gln Ser Pro Val Leu Val Ile Tyr
        35                  40                  45

Gln Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Val Trp Asp Asn Tyr Ser Val Leu
                85                  90                  95

Phe Gly Gly Gly Thr Lys Leu Thr Val Leu
                100                 105
```

COMBINATION OF A CD30XCD16 ANTIBODY WITH A PD-1 ANTAGONIST FOR THERAPY

RELATED APPLICATIONS AND INCORPORATION BY REFERENCE

This application is a Continuation-in-Part Application of International Patent Application PCT/EP2016/060113 filed May 4, 2016, which published as PCT Publication No. WO 2016/177846 on Nov. 10, 2016, which claims benefit of European Patent Applications No. 15166303.6 filed May 4, 2015 and 16152650.4 filed Jan. 25, 2016.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on Oct. 18, 2017, is named 43488002004_SL.txt and is 8,838 bytes in size.

FIELD OF THE INVENTION

The invention relates to a combination of (i) a multifunctional antibody having specificity for CD30 on a tumor cell and having specificity for CD16, in particular CD16A, on a natural killer (NK)-cell and (ii) a PD-1 antagonist, e.g. anti-PD-1 antibody, for the treatment of a tumor, in particular Hodgkin lymphoma (HL).

BACKGROUND OF THE INVENTION

Because, NK-cells mediate innate immunity and are constitutively activated, they are candidates for cancer immunotherapy. A bispecific CD30/CD16A tandem diabody (TandAb®) binds NK-cells via CD16A and has a second binding domain for CD30, a cancer-specific target, e.g CD30$^+$ Hodgkin Reed-Sternberg (HRS) lymphoma cells. Such tandem diabody recruits and redirects the NK-cells to CD30$^+$ tumor cells and binds both targets with high affinity, establishing a bridge whereby the NK-cells are activated and redirected to kill the tumor cells. Higher cytotoxic potency relative to native and Fc-enhanced antibodies has been reported for this bispecific CD30/CD16A tandem diabody (see Reusch U. et al., MABS. 2014; 6(3):727-738). The CD30/CD16A tandem diabody is well tolerated and active in Hodgkin lymphoma patients (see Rothe A. et al., Blood. 2015; 125(26):4024-4031). Despite these promising results further improvements for this tumor-targeted NK-cell engaging immunotherapy are desired.

Immune checkpoint molecules are cell surface proteins, e.g. receptors that regulate costimulatory or coinhibitory pathways of the immune response. Examples of immune checkpoint molecules are cytotoxic T-lymphocyte antigen-4 (CTLA-4), programmed death-1 (PD-1), programmed death ligand-1 (PD-L1) or programmed death ligand-2 (PD-L2), immune costimulatory molecules on NK-cell and costimulatory receptors of the TNF receptor family, for example CD137.

PD-1 (PDCD1 or CD279) receptor mediates a coinhibitory pathway. Further PD-1 binds to PD-L1 which induces a coinhibitory signaling upon receptor-ligand ligation. PD-1 pathway is a checkpoint to limit T-cell mediated immune response (Keir M E et al., Annu. Rev. Immunol. 2008; 26:677-704). By expressing PD-1 ligands on the cell surface and engaging PD-1$^+$ immune effector cells, tumors can co-opt the PD-1 pathway to evade an immune response (Weber J, Semin Oncol. 2010; 37:430-9; Ansell S et al., N. Engl J. Med. 2015; 372:311-319). PD-1 antagonists blocking the interaction between PD-1 and PD-L1, which is implicated in the down-modulation of T-cell responses have been studied in a variety of cancers and combinations of PD-1 blockade with CTLA-4 blockade for regulating adaptive immunity has been suggested (Dolan D and Gupta S, Cancer Control. 2014; 21:231-237). The anti-PD-1 antibody pembrolizumab has demonstrated initial clinical efficacy in single arm monotherapy trials in patients with Hodgkin lymphoma as determined by response rate. Ongoing clinical trials are being conducted in these tumor types as well as a number of other advanced solid tumor indications and hematologic malignancies.

Further, anti-CD137 antibodies which bind to the costimulatory molecule CD137 on NK cells have been used in combination with other monoclonal antibodies like rituximab or lenalidomide for enhancing NK-cell function (Miller J., Hematology 2013:247-253).

Citation or identification of any document in this application is not an admission that such document is available as prior art to the present invention.

SUMMARY OF THE INVENTION

Provided herein is a combination of a multifunctional antibody having specificity for CD30 and CD16, in particular CD16A, and a PD-1 antagonist, in particular an anti-PD-1 antibody for use in a method of treating a tumor, in particular Hodgkin lymphoma (HL). This combination results in an enhanced tumor cell killing, because the combination of an NK-cell engaging and tumor targeting multifunctional antibody with the immune modulating agent has a synergistic anti-tumor effect through an integrated immune response involving NK-cells, T-cells, macrophages and dendritic cells. Hence, all immune subpopulations are activated and induced to infiltrate the tumors by the combination treatment. A combination of CD30/CD16A bispecific antibody and anti-PD-1 antibody significantly enhances the initial innate immune response by enhanced tumor infiltration of the innate immune cells, in particular NK-cells, macrophages and dendritic cells.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

DETAILED DESCRIPTION OF THE INVENTION

In preclinical animal studies of Hodgkin lymphoma using autologous patient material, i.e. patient derived xenograft (PDX) and immune cells from blood (PBMC) from the same donor, the established tumor was treated with a bispecific CD30/CD16 antibody in combination with an agent modulating an anti-PD1 antibody both alone and in combination. While the single agent treatment showed a significant reduction in tumor growth for most molecules when compared to the control treatment group (irrelevant IgG), the combination of bispecific CD30/CD16 multifunctional antibody and anti-PD-1 antibody showed enhanced anti-tumor efficacy. Compared to IgG treatment it was observed that in animals treated with combinations of CD30/CD16 antibody and an anti-PD-1 antibody the NK cell population in the tumor increased. As early as 2 days after treatment (day 30) bispecific CD30/CD16A tandem diabody monotherapy induced an infiltration of both NK cells and macrophages in the tumors. This effect was enhanced over time and both immune cell populations demonstrated strong bispecific CD30/CD16A tandem diabody-medicated infiltration of the tumors towards the end of the experiment (day 58). When bispecific CD30/CD16A tandem diabody was combined with the immuno-modulating antibody anti-PD-1 the effect on innate immunity was initially driven by bispecific CD30/CD16A tandem diabody alone, but the anti-PD-1 treatment did result in a more pronounced innate cell infiltration at the end of the experiment. In addition, while there was a small increase of T-cells in animals treated only with CD30/CD16 antibody, the cytotoxic T-cells detected in animals treated with CD30/CD16 antibody in combination with an agent modulating an immune checkpoint molecule increased.

Figure 8A:
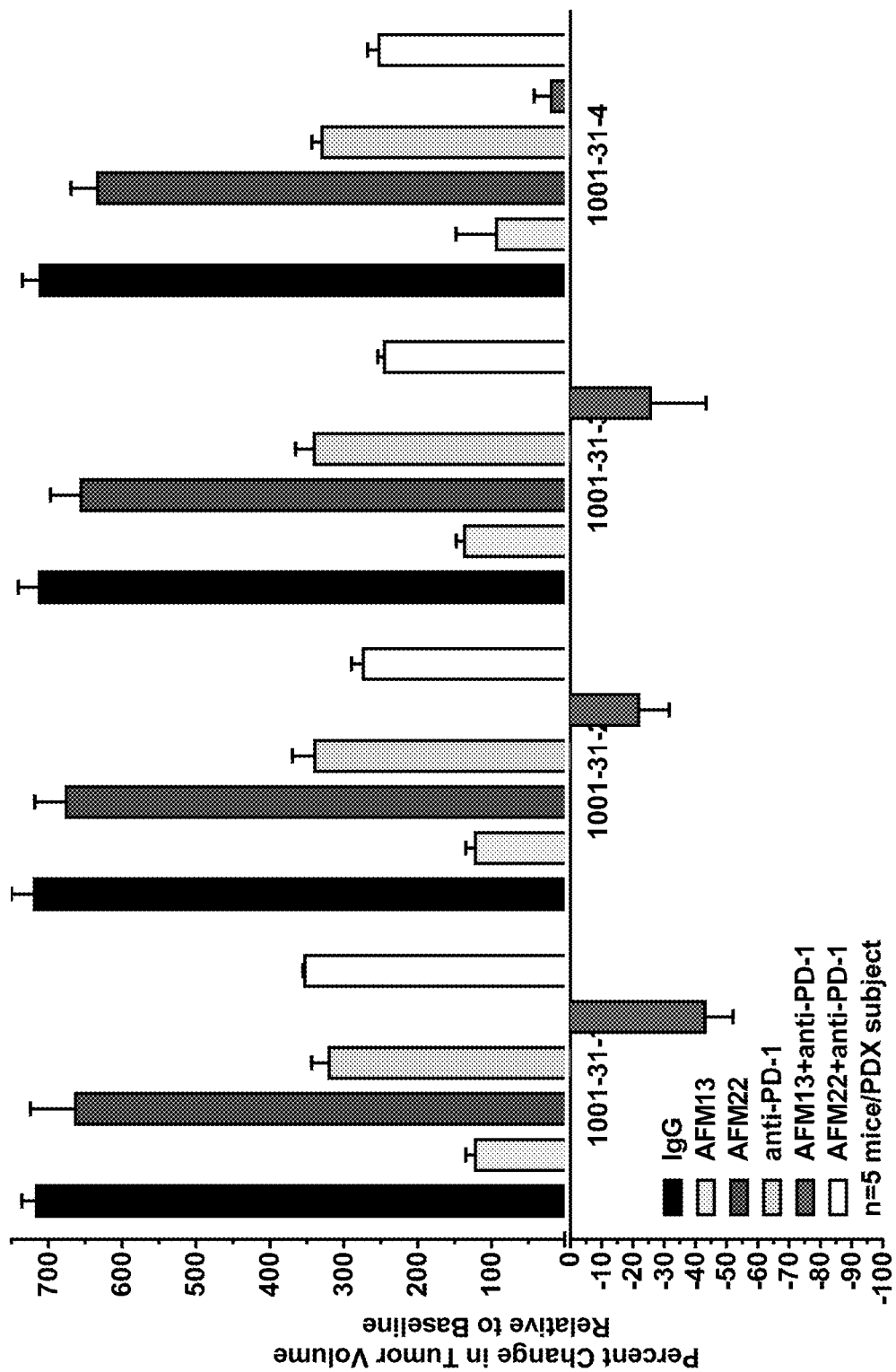
FIGS. 8A-B shows results of four in vivo PDX models at day 58: (A) tumor sizes; IgG designates an irrelevant control IgG antibody, AFM13 designates a CD30/CD16A tandem diabody, AFM22 designates an irrelevant control tandem diabody (EGFRvIII/CD16A), anti-PD-1 designates pembrolizumab; (B) Intratumoral lymphocyte populations
Figure 8B:
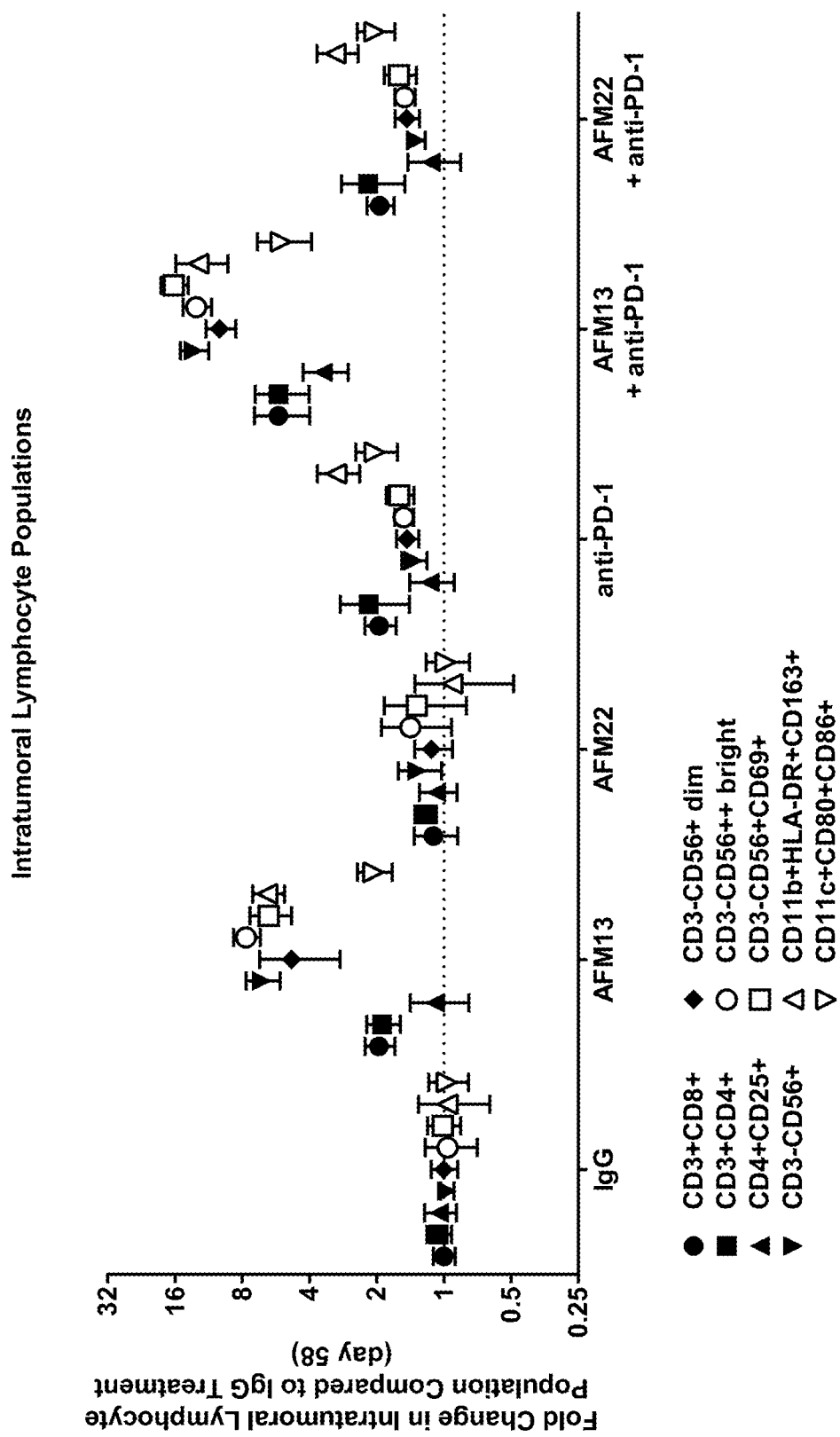

While monotherapy with anti-PD-1 induces T-cell infiltration to a certain extent, CD30/CD16 antibody in combination with an anti-PD-1 enhanced the infiltration of both CD4+ and CD8+ T-cell in tumors. T-cells and dendritic cells were significantly induced by the combination of CD30/CD16 antibody and anti-PD-1 compared to either monotherapy of CD30/CD16 antibody or anti-PD-1 (FIG. 8B). Combination of CD30/CD16 antibody and anti-PD-1 advantageously induced an infiltration of dendritic cells into the tumor shortly after the administration (day 30 and day 40). The combination of CD30/CD16 antibody and anti-PD-1 significantly increased the tumor infiltration of all immune subpopulations, such as T-cells, NK-cells, macrophages and dendritic cells, compared to monotherapies by CD30/CD16 antibody and anti-PD-1, respectively (FIG. 8B).

Therefore, the combination of (i) a multifunctional antibody having specificity for CD30 and having specificity for CD16, in particular CD16A and (ii) an anti-PD-1 antibody, increases synergistically the killing of tumor cells which results in a significantly increased tumor regression. The remarkable tumor regression is achieved by the coordinated, i.e. integrated, action of all immune subpopulations, such as CD4+ and CD8+ T-cells and NK-cells, macrophages and dendritic cells as well as the intra-tumoral increase of inflammatory cytokines, such as in particular IFN-γ, through the combined activity of the NK-cell engaging multifunctional antibody and the agent modulating the immune checkpoint molecule. The combination therapy provided herein demonstrates for the first time that the efficacy of inducing an innate immune response by a NK-cell engaging and tumor targeting antibody can be augmented by an anti-PD-1 antibody which is known for stimulating the adaptive immune response by blocking the PD-1 pathway.

The combination of the multifunctional antibody having specificity for CD30 and CD16, in particular CD16A, and the PD-1 antagonist, in particular PD-1 antibody, is used for increasing the innate immune response as compared with that of the multifunctional antibody having specificity for CD30 and CD16A alone in a method of treating a tumor, in particular Hodgkin lymphoma (HL). In particular, the innate immune response is increased by cell infiltration of innate cells, in particular macrophages, dendritic cells and NK-cells into the tumor. Further, the intratumoral infiltration of CD4+ and CD8+ T-cells is increased.

"Innate immune response" refers to the activation of one or more innate leukocytes of the innate immune system (or nonspecific immune system or in-born immunity system). The activated leukocytes of the innate immune response comprise Natural killer (NK) cells, macrophages and dendritic cells. The innate immune system is distinct from the adaptive immune system (or specific immune system) which includes lymphocytes like CD4+ or CD8+ T-cells.

"Combination" refers to a combination therapy, combined therapy or polytherapy that uses more than one medication for the treatment of a tumor, i.e. single disease. In the present invention "combination" is used for a combination therapy that embraces the steps of administering a multifunctional antibody having specificity for CD30 and CD16A, e.g. bispecific CD30/CD16A tandem diabody, and a PD-1 antagonist, e.g. anti-PD-1 antibody, for the treatment of a tumor, e.g. Hodgkin lymphoma. Hence, the bispecific CD30/D16A tandem diabody and the anti-PD-1 antibody are given in combination. In contrast, "monotherapy" refers to a therapy which embraces the administration of a single medication alone, e.g. either bispecific CD30/CD16A tandem diabody or anti-PD-1 antibody.

The combination comprises a multifunctional antibody for use in a NK-cell based immunotherapy of a tumor. The term "multifunctional" as used herein means that the antibody exhibits two or more different biological functions. For example, the different biological functions are different specificities for different antigens. In certain instances, the multifunctional antibody is multispecific, e.g. bispecific, trispecific, etc. Such multispecific, e.g. bispecific, binding proteins include, for example, bispecific monoclonal antibodies of the classes IgA, IgD, IgE, IgG or IgM, as well as antibody fragments or antibody derivatives including, for example, Fab, Fab', F(ab')$_2$, Fv fragments, single-chain Fv, tandem single-chain Fv (scFv)$_2$, dual affinity retargeting antibodies (DART™), diabody and tandem diabody (TandAb®), single-chain diabodies (scDb) and flexibodies. The term "antibody" as used herein means monoclonal antibodies as well as antibody fragments and antibody derivatives comprising an antibody binding domain. Various antibody formats can be generated from antibody fragments and antibody derivatives which have similar antibody binding specificity as a native antibody, but differ in validity and effector function due to the number of binding domains or lack of Fc-region. Examples of antibody formats for bispecific antibodies are described in Spiess, C. et al., Mol Immunol. 2015 October; 67(2 Pt A):95-106 and Kontermann, R. E., Brinkmann, U., Drug Discov. Today 2015 July; 20(7):838-47.

In certain embodiments the multifunctional antibody is a multispecific, e.g. bispecific tandem diabody (TandAb®). A tandem diabody is constructed by linking the four variable domains of the heavy and light chains (VH and VL) from two or more different Fv binding domains in a single polypeptide. The domains are positioned such that corresponding VH and VL can pair when two molecules of the polypeptide align in a head-to-tail fashion. Short linkers between the domains (twelve or fewer amino acids) prevent intramolecular pairing of the Fv. The antibody format of a tandem diabody and its manufacture is described in Weichel et al., European Pharmaceutical Review 2015, vol. 20:27-32, Kipriyanov S M: Methods Mol. Biol. 2009; 562:177-93 or Kipriyanov S M: Methods Mol Biol 2003; 207:323-33.

In certain embodiments first the multifunctional antibody, e.g. bispecific CD30/CD16A tandem diabody, is administered and subsequently the agent being an immunomodulatory molecule, i.e. anti-PD-1 antibody, is administered. Hence, CD30/CD16A and anti-PD-1 antibody can be sequentially administrated, typically over a certain period of time. Administration of the multifunctional antibody and the anti-PD-1 can be effected by different ways, e.g. by intravenous, intraperitoneal, subcutaneous, intramuscular, topical or intradermal administration. In some embodiments, the route of administration depends on the kind of therapy and the kind of compound contained in the pharmaceutical composition. The dosage regimen will be determined by the attending physician and other clinical factors. Dosages for any one patient depends on many factors, including the patient's size, body surface area, age, sex, the particular compound to be administered, time and route of administration, the kind of therapy, general health and other drugs being administered concurrently. An "effective dose" refers to amounts of the active ingredient that are sufficient to affect the course and the severity of the disease, leading to the reduction or remission of such pathology. An "effective dose" useful for treating a tumor may be determined using known methods. Hence, the invention encompasses a method of treatment, i.e. combination therapy, comprising the step of administering to a subject suffering from a CD30$^+$ tumor, e.g. Hodgkin lymphoma, effective dosages of a combination of a multifunctional antibody and an anti-PD-1 (PD-1 antibody), wherein the multifunctional antibody has specificity for CD30 and CD16, e.g. is a CD30/CD16A antibody.

This immunotherapeutic approach of antibody-mediated recruitment of NK-cells to tumors using multifunctional antibodies can be used for the treatment of tumors, for example Hodgkin lymphoma. Therefore, the invention provides a combination of a multifunctional antibody having specificity for CD30 and CD16A, e.g. bispecific CD30/CD16A tandem diabody, and an anti-PD-1 antibody for use in a combination therapy for treating a tumor, e.g. Hodgkin lymphoma or anaplastic large-cell lymphoma (ALCL).

In certain embodiments the multifunctional antibody recruits NK-cells by binding exclusively to the CD16 isoform CD16A. Examples of anti-CD16A binding domains and their generation are described in WO 2006/125668. In certain embodiments the anti-CD16A binding domain comprises CDR1, CDR2 and CDR3 of the heavy chain variable domain set forth in SEQ ID NO:4 and CDR1, CDR2 and CDR3 of the light chain variable domain set forth in SEQ ID NO:5. In particular embodiments the anti-CD16A binding domain comprises the heavy chain variable domain set forth in SEQ ID NO:4 and the light chain variable domain set forth in SEQ ID NO:5.

Examples of CD30 antibody binding domains suitable for the multifunctional antibody according to the invention are disclosed in Arndt M A et al., Blood. 1999; 94:2562-8; Schlapschy M. et al., Protein Eng Des Sel. 2004; 12:847-60 and Reusch U. et al., MABS. 2014; 6(3):727-738. In certain embodiments the anti-CD30 binding domain is a modified anti-CD30 IgG HRS-3 (Reusch U. et al., 2014) and comprises CDR1, CDR2 and CDR3 of the heavy chain variable domain set forth in SEQ ID NO:2 and CDR1, CDR2 and CDR3 of the light chain variable domain set forth in SEQ ID NO:3. In particular embodiments the anti-CD30 has the Fv binding domains of a modified anti-CD30 IgG HRS-3 (Reusch U. et al., 2014) and comprises the heavy chain variable domain set forth in SEQ ID NO:2 and the light chain variable domain set forth in SEQ ID NO:3.

In a certain embodiment of the invention the multifunctional antibody is a bispecific, tetravalent tandem diabody CD30/CD16A, which is a homodimer of two non-covalently associated polypeptide chains, wherein each of the tandem diabody polypeptide chains has the amino acid sequence set forth in SEQ ID NO:1. Example 1 describes the CD30/CD16A tandem diabody which specifically recruits NK cells by binding exclusively to the isoform CD16A. Tandem diabodies have two binding sites for each antigen, but no Fc domains. The CD30/CD16A tandem diabody of example 1 has a molecular weight of about 104 kDa and can be produced in bacteria or in mammalian cells, e.g. CHO. It specifically targets CD30 on Hodgkin lymphoma cells and recruits and activates NK-cells by binding to CD16A. The construction and production of this tandem diabody is described in Reusch U. et al., MABS. 2014; 6(3):727-738 and the efficacy of this CD30/CD16A tandem diabody is reported in Rothe A. et al., Blood. 2015; 125(26):4024-4031.

In certain embodiments the PD-1 antagonist is a PD-1 antibody or a PD-L1 antibody. Examples of PD-1 antibodies (anti-PD-1 or anti-PD-1 antibody) include nivolumab, pembrolizumab (MK3475, Keytruda) and an example of PD-L1 antibody (anti-PD-L1 or anti-PD-L1 antibody) is pidilizumab.

The combination of a multifunctional CD30/CD16 antibody, e.g. bispecific, CD30/CD16A antibody, and anti-PD-1 antibody, can be used for treating CD30+ tumors, such as, for example, Hodgkin lymphoma or anaplastic large-cell lymphoma (ALCL).

In certain embodiments first the CD30/CD16 antibody, e.g. CD30/CD16A, for example bispecific CD30/CD16A tandem diabody, is administered and subsequently anti-PD-1 antibody is administered. For example, anti-PD-1 antibody is administered, 10-72 h, e.g. 1 day, after the administration of the CD30/CD16 antibody, for example bispecific CD30/CD16A tandem diabody.

In certain embodiments the combination, i.e. combination therapy, comprises the administration of a further agent for modulating another immune checkpoint molecule, for example an antagonistic antibody blocking a coinhibitory pathway or an agonistic antibody inducing a costimulatory pathway through binding to the respective immune checkpoint molecule. Such antibodies are also known as checkpoint inhibitors (CPI) or checkpoint agonists (CPA) and have been described and clinically tested.

Examples of another immune checkpoint molecules for the combination, i.e. combination therapy, are CTLA-4 and CD137.

CTLA-4 induces a signal that inhibits T-cell response. Examples of CTLA-4 antibodies for the combination are ipilimumab and tremelimumab.

CD137 (4-1BB) or TNF receptor superfamily 9 (TNFRSF9) is a costimulatory receptor that belongs to the TNF receptor superfamily, a member of tumor necrosis factor receptor superfamily which is involved in the regulation of the activation of immune cells. The functional role of CD137 is enhancing cytotoxic T cell responses. An example of a CD137 agonistic antibody which enhances the T cell response is urelumab.

In certain embodiments the combination, i.e. combination therapy, according to the invention further comprises an antibody selected from the group consisting of anti-CTLA4 antibody and anti-CD137 antibody.

In a particular embodiment, both antibodies anti-PD-1 antibody and anti-CD137 antibody are administered in combination with the bispecific CD30/CD16 antibody. Hence, in this certain embodiment the combination, i.e combination therapy, comprises the steps of administering a bispecific CD30/CD16A, an anti-PD-1 and an anti-CTLA4.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

Example

CD137 Co-Stimulation and/or Blocking PD-1 Enhances NK-Cell-Mediated Target Cell Lysis by Bispecific CD30/CD16A Tandem Diabody Methods:

Efficacy was assessed in vitro with human PBMCs, enriched NKs, and CD30+ target cells as well as cell line and patient-derived xenograft in vivo models with CD30/CD16A tandem diabody, anti-CTLA-4, anti-PD-1, or anti-CD137 antibodies.

To evaluate NK-cell cytotoxicity for CD30+ lymphoma cell lines, chromium release was performed as follows: PBMCs were cultured for 24 hours together with anti-CD30 (10 µg/mL) and irradiated (5,000 rads) CD30+ lymphoma tumor cells at a ratio of 1:1. After 24 hours, NK-cells were isolated from these cultures by negative magnetic cell sorting using NK-cell isolation beads (Miltenyi Biotec) according to manufacturer's instructions. NK-cells were assessed for purity (>90% purity as defined by flow cytometry) prior to chromium release assay. Target cells were labeled with 150 µCi $^{51}$Cr per 1×10$^6$ cells for 2 hours. Percent lysis was determined after 4 hour cultures of pre-activated, purified NK-cells at variable effector:target cell ratios with $^{51}$Cr-labeled lymphoma cells in media alone, or with single or multiple antibodies.

Xenografted tumor pieces (8×8 mm) derived from a surgical specimen of a newly diagnosed patient with CD30+ lymphoma (including Hodgkin Disease), in Rag2$^{-/-}$ IL2Rγ$^{null}$ mice (n~100) were observed for engraftment and up to 80 mice with engraftment of similar size (0.5 cm$^2$) randomized into up to 8 groups on day 28. Autologous PBMCs were infused on day 28 (2×10$^6$ PBMCs/mouse) intra-peritoneally. Therapy begins on day 28 and is continued weekly for a total of three intraperitoneal injections, all dosed at 15 mg/kg. With combination therapy, anti-CD30/CD16A (AFM13; Reusch U. et al., MABS. 2014; 6(3):727-738) was dosed on day 28 and anti-CTLA4 (Ipilimumab), anti-CD137 (Urelumab) or anti-PD1 (Pembrolizumab) dosed on day 29. Tumor size was compared between groups at day 56. All mice are sacrificed for immunophenotyping once a group requires euthanasia due to growth to 700% of original tumor size (app 3.5 cm$^2$) on day 58.

Figure 6A:
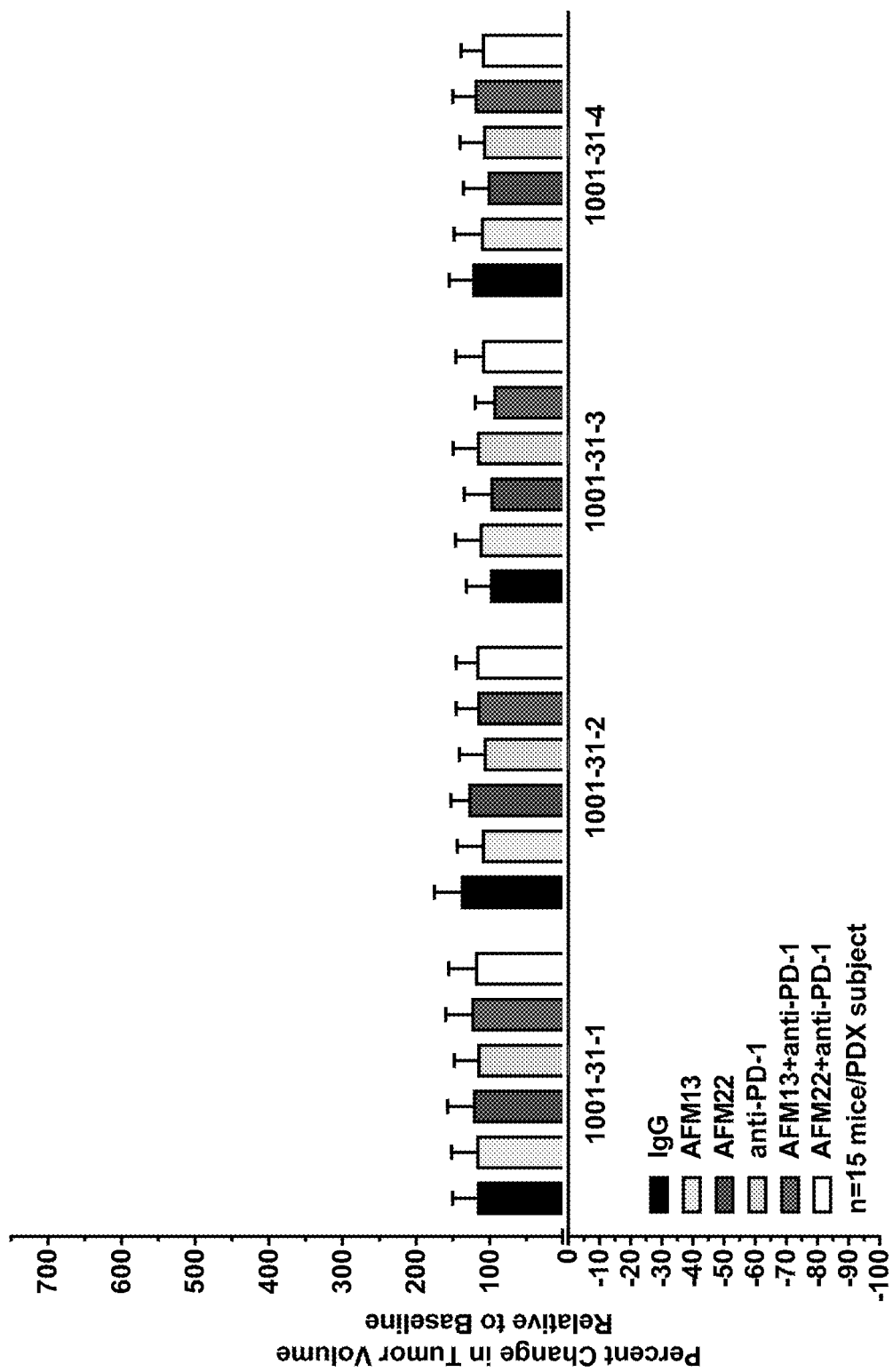
FIGS. 6A-B shows results of four in vivo PDX models at day 30: (A) tumor sizes; IgG designates an irrelevant control IgG antibody, AFM13 designates a CD30/CD16A tandem diabody, AFM22 designates an irrelevant control tandem diabody (EGFRvIII/CD16A), anti-PD-1 designates pembrolizumab; (B) Intratumoral lymphocyte populations
Figure 6B:
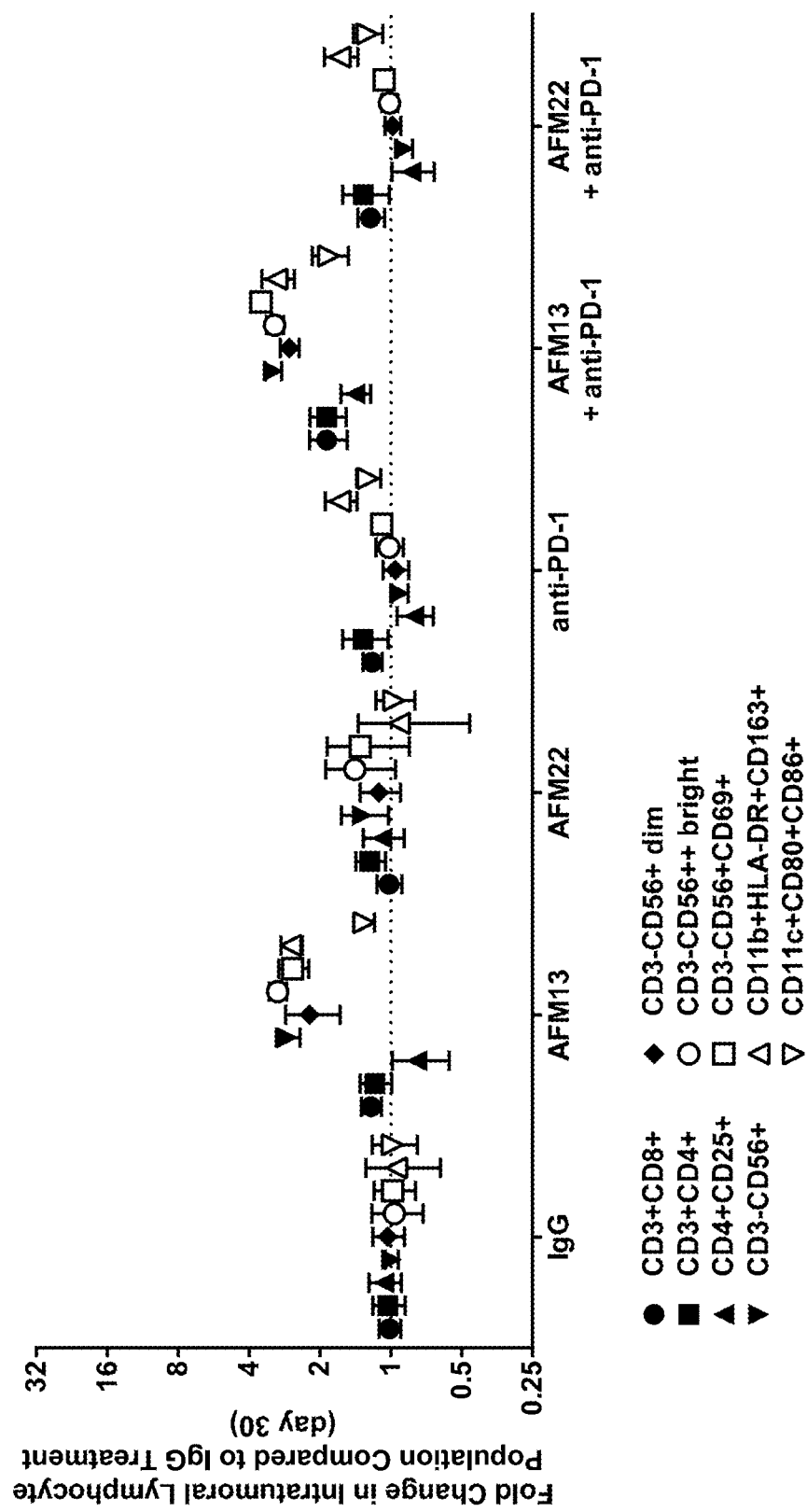
Figure 7A:
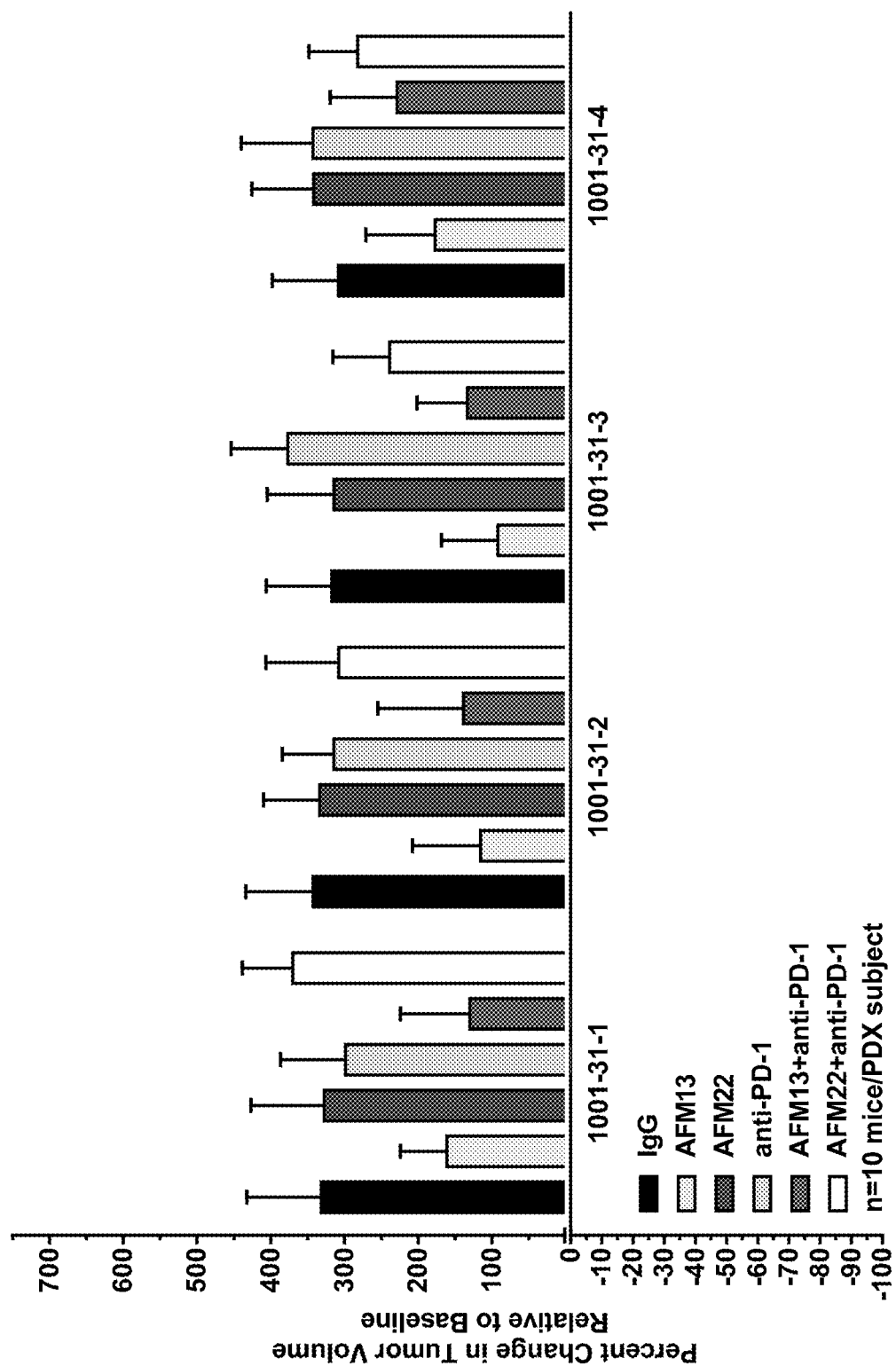
FIGS. 7A-B shows results of four in vivo PDX models at day 44: (A) tumor sizes; IgG designates an irrelevant control IgG antibody, AFM13 designates a CD30/CD16A tandem diabody, AFM22 designates an irrelevant control tandem diabody (EGFRvIII/CD16A), anti-PD-1 designates pembrolizumab; (B) Intratumoral lymphocyte populations
Figure 7B:
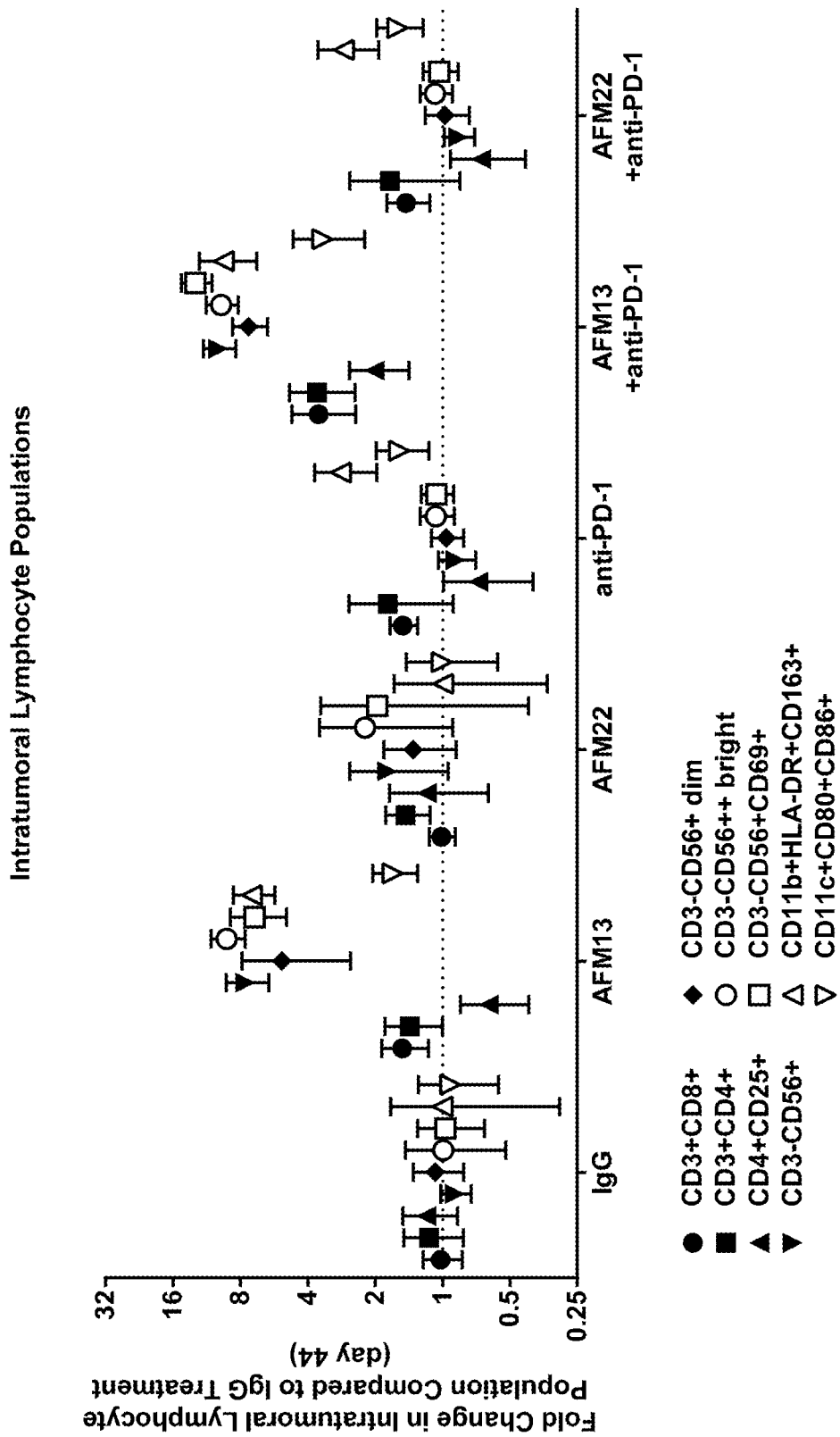

Tumor infiltrating human lymphocytes, myeloid cells and intratumoral cytokines were evaluated on days 30, 44, and 58, i.e. 2, 16 and 30 days after treatment start. The following biomarkers were determined: NK-cell infiltration was determined as CD3$^-$ and CD56$^+$; T-cell infiltration was determined as CD25$^+$, and CD4$^+$, CD3$^+$ and CD4$^+$, CD3$^+$ and CD8$^+$; NK-cell subsets are determined as CD56dim, CD56bright, CD16A, CD69; macrophages are determined as CD11b, HL-DR and CD163; dendritic cells by CD11c, CD80 and CD86 (FIGS. 6B, 7B and 8B).

The CD30/CD16A tandem diabody is the antibody AFM13 described in Reusch U. et al., MABS. 2014; 6(3): 727-738. The CD30/CD16A tandem diabody comprises the anti-CD30 domain of hybridoma HRS-3 and its construction and expression in bacteria is disclosed in example 19 of WO 2006/125668.

Figure 1:
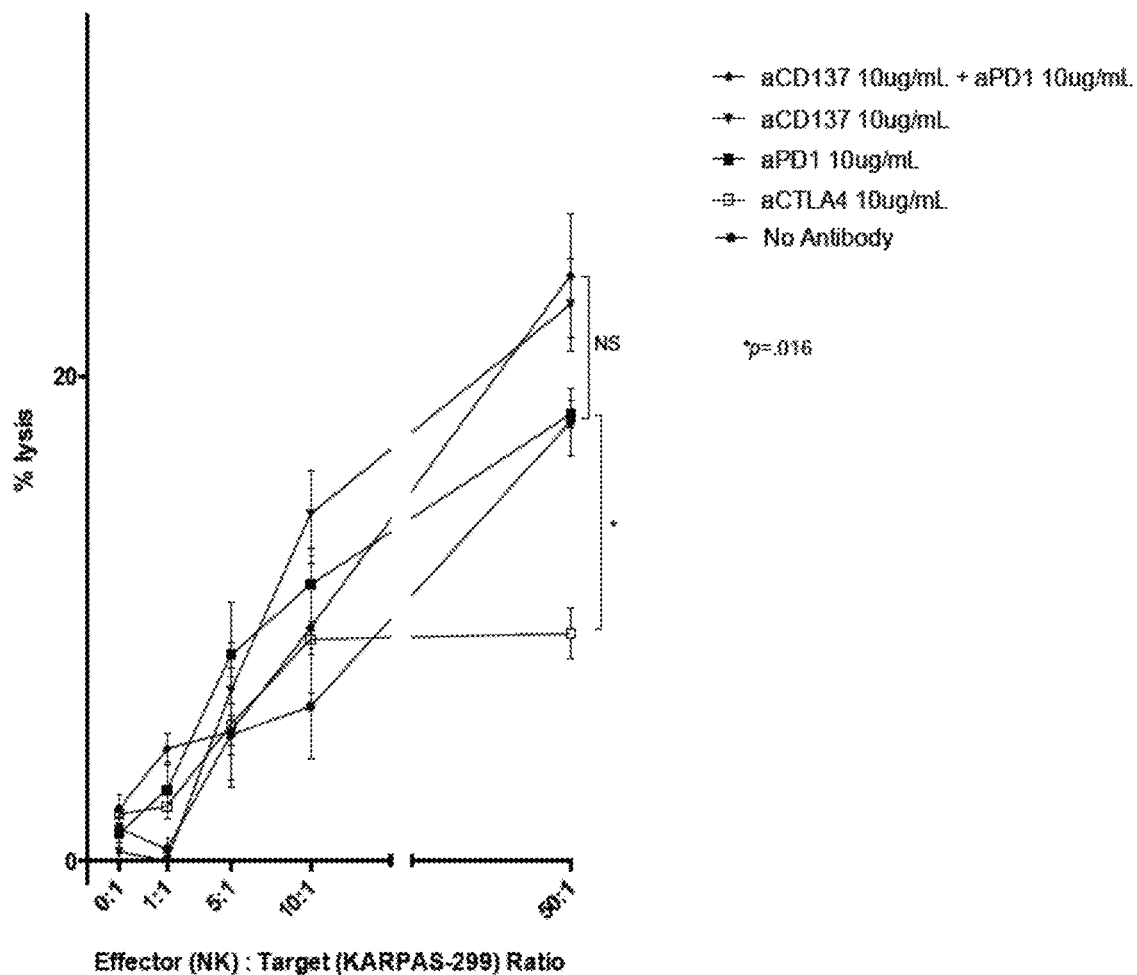
FIG. 1 shows a chromium release assay. Percent lysis was determined after cultures of pre-activated, purified NK-cells at variable effector:target cell (KARPAS-299) ratios with $^{51}$Cr-labeled lymphoma cells in media alone (no antibody), or with single (aCD137, aPD1, aCTLA4) or multiple antibodies (aCD137 and aPD1), wherein "a" is an abbreviation of "anti".
Figure 2:
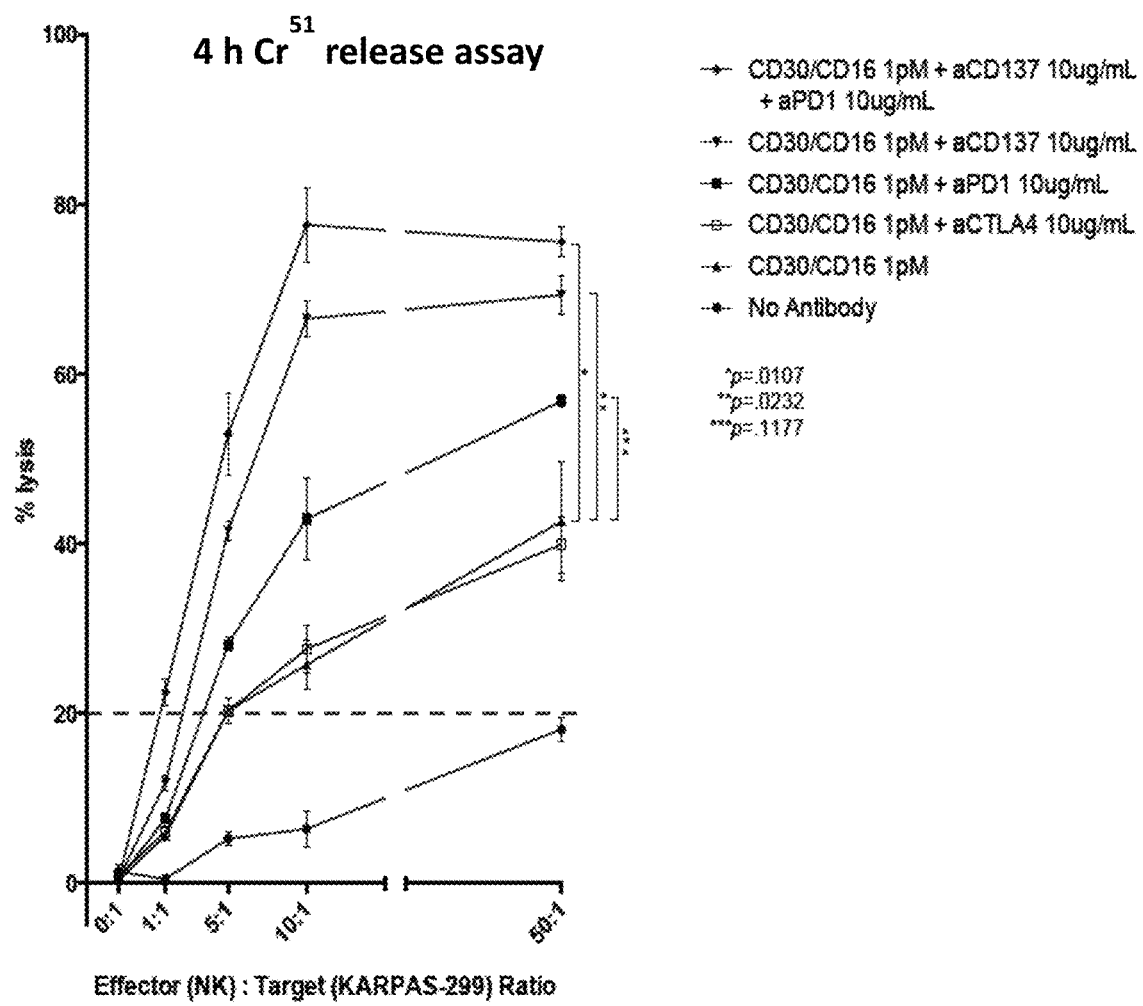
FIG. 2 shows a chromium release assay. Percent lysis was determined after cultures of pre-activated, purified NK-cells at variable effector:target cell (KARPAS-299) ratios with $^{51}$Cr-labeled lymphoma cells in media alone (no antibody), or with single (aCD137, aPD1, aCTLA4) or multiple antibodies (aCD137 and aPD1), CD30/CD16A tandem diabody was used at 1 pM concentrations, wherein "a" is an abbreviation of "anti".
Figure 3:
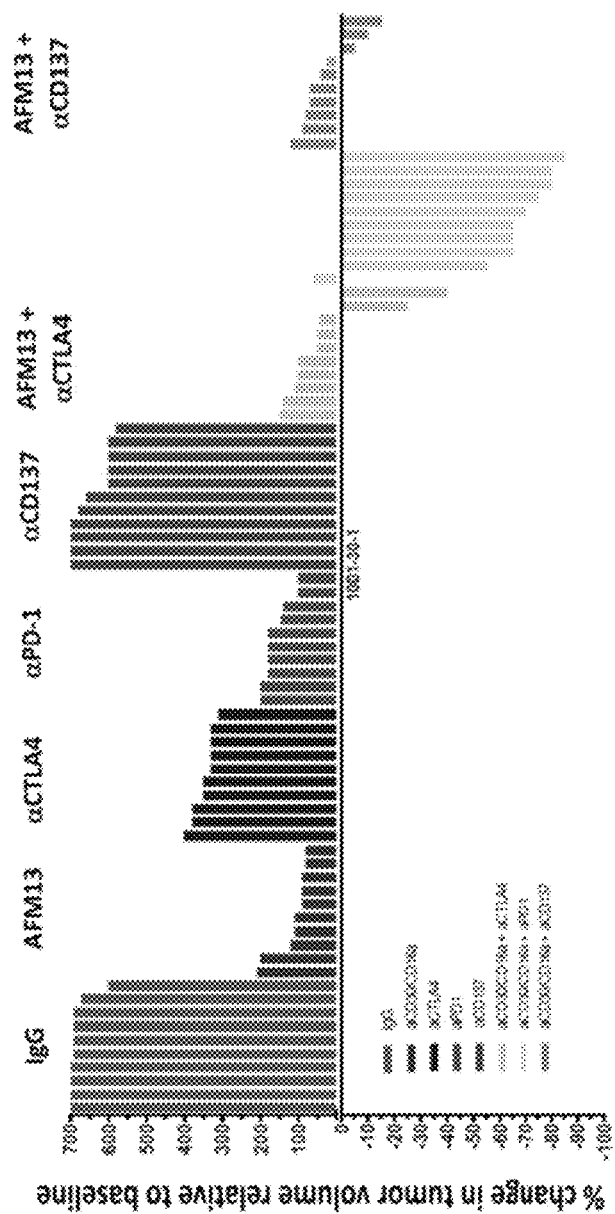
FIG. 3 shows results of an in vivo PDX model. AFM13 designates a CD30/CD16A tandem diabody.
Figure 4:
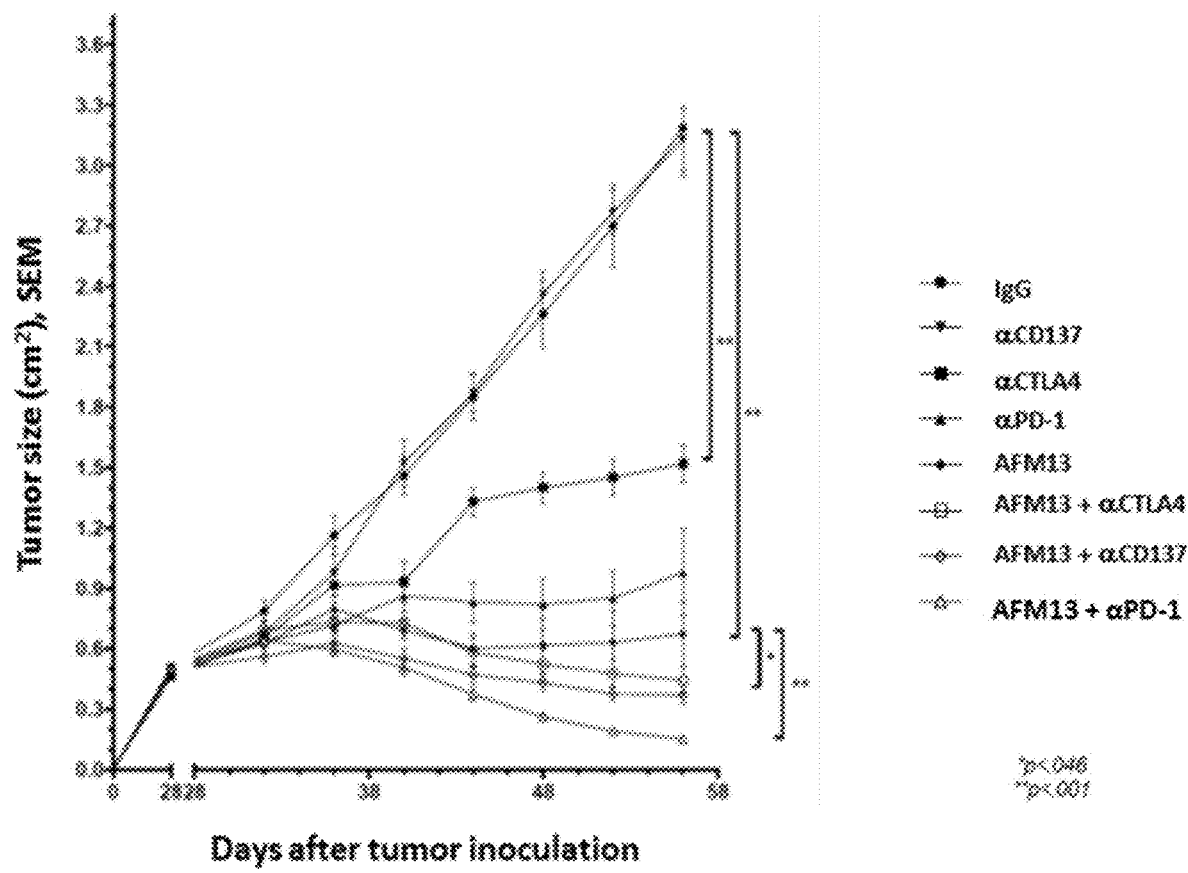
FIG. 4 shows results of an in vivo PDX model. AFM13 designates the CD30/CD16A tandem diabody.

Results:

CD30/CD16A tandem diabody demonstrated higher potency and efficacy toward target and effector cells relative to other CD30$^+$ antibody formats (EC$_{50}$=15 pM). These favorable properties resulted in superior cytotoxicity when CD30/CD16A tandem diabody was incubated with CD30$^+$ tumor cells and enriched NK-cells (FIG. 2). Single treatment with CD30/CD16A tandem diabody at suboptimal concentrations (1 pM) induced effector-to-target cell-dependent lysis of CD30$^+$ lymphoma cells up to 40% using enriched NK-cells. Immune-modulating antibodies alone mediated substantially lower lysis (<25%) (FIG. 1). However, the addition of anti-PD-1 or anti-CD137 to CD30/CD16A tandem diabody strongly enhanced specific lysis up to 70%, whereas the addition of anti-CTLA-4 to CD30/CD16A tandem diabody showed no beneficial effect. The most impressive increase of efficacy was observed when CD30/CD16A tandem diabody was applied together with a combination of anti-PD-1 and anti-CD137 (FIG. 2). In vivo, synergy of CD30/CD16A tandem diabody and immune modulating antibody combination was observed with each immune modulating antibody tested and augmented with anti-PD1 (regression in 9/10 tumors), anti-CTLA-4 (3/10), and anti-CD137 mAb (3/10) and influenced by presence of regulatory T-cells, NK-cells, and Th1 cytokines (FIGS. 3 and 4).

Figure 5:
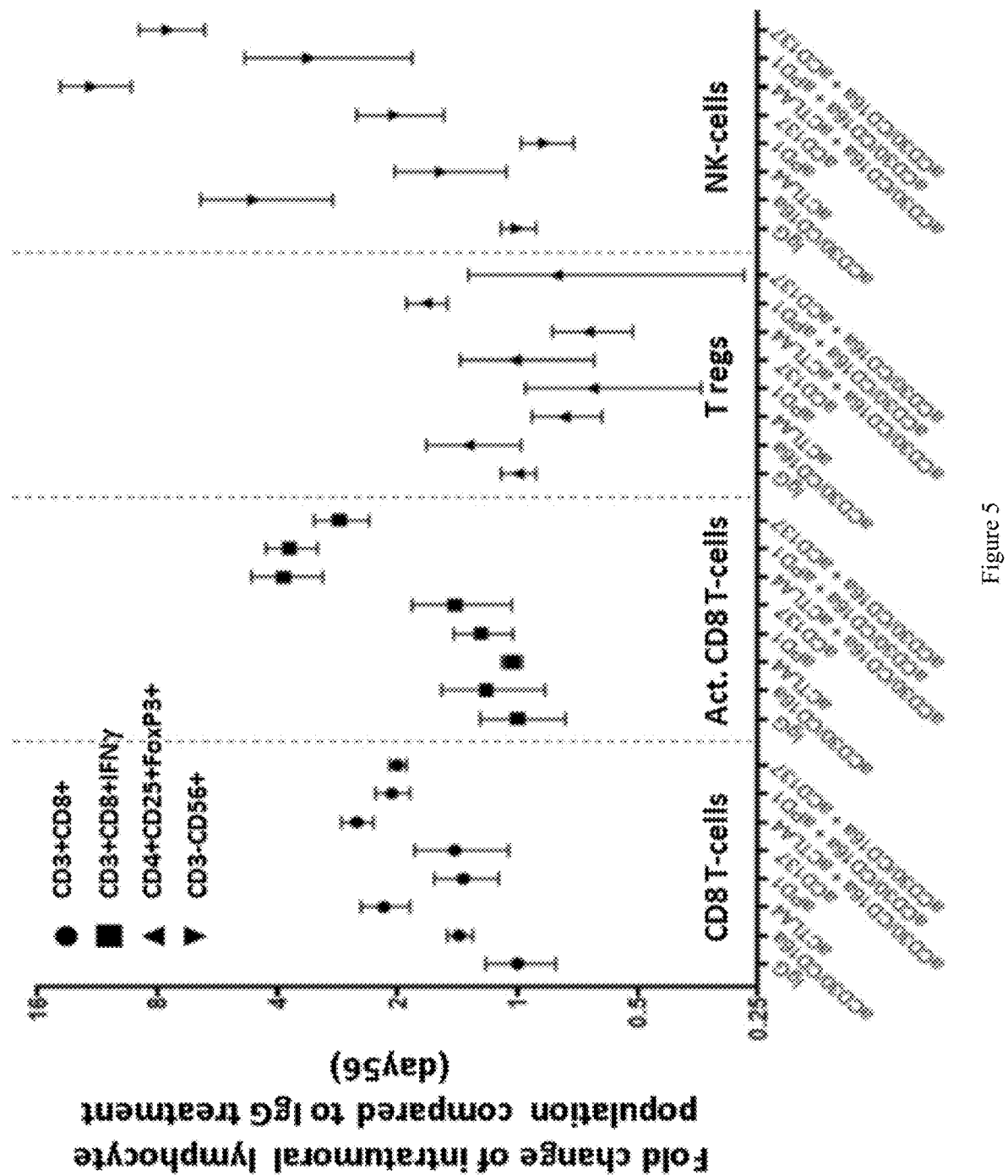
FIG. 5 In vivo PDX model: increased lymphocytes in CD30/CD16A tandem diabody treated mice

Compared to IgG treatment it was observed that in animals treated with combinations of CD30/CD16A tandem diabody and anti-CTLA-4, anti-PD-1 and anti-CD137 the NK-cell population in the tumor increased. In addition, while there was no increase of T-cells in animals treated only with CD30/CD16A tandem diabody or anti-CTLA-4, anti-PD-1 and anti-CD137 alone, the cytotoxic T-cells detected in animals treated with CD30/CD16A tandem diabody in combination with anti-CTLA-4, anti-PD-1 and anti-CD137 increased (FIG. 5).

The findings support that dual-antibody therapy augments the efficacy of CD30/CD16A tandem diabody and immune modulating antibodies achieving a remarkable tumor regression.

The enhanced antitumor activity of the CD30/CD16A tandem diabody in combination with immune-modulating antibodies was associated with higher numbers of tumor-infiltrating NK- and T-cells and augmented release of pro-inflammatory cytokines. Treatment with control IgG or irrelevant CD16A-recruiting tandem diabodies did not induce an unspecific immune cell activation supporting strict target-dependent NK-cell activation by CD30/CD16A tandem diabody. Combination of CD30/CD16A tandem diabody with immune-modulating anti-CTLA-4, anti-CD137, and anti-PD-1 antibodies not only enhanced the anti-tumor activity of NK-cells but also stimulated infiltration of T-cells and cytokine release in the tumors supporting cross-talk between innate and adaptive immunity.

Figure 9:
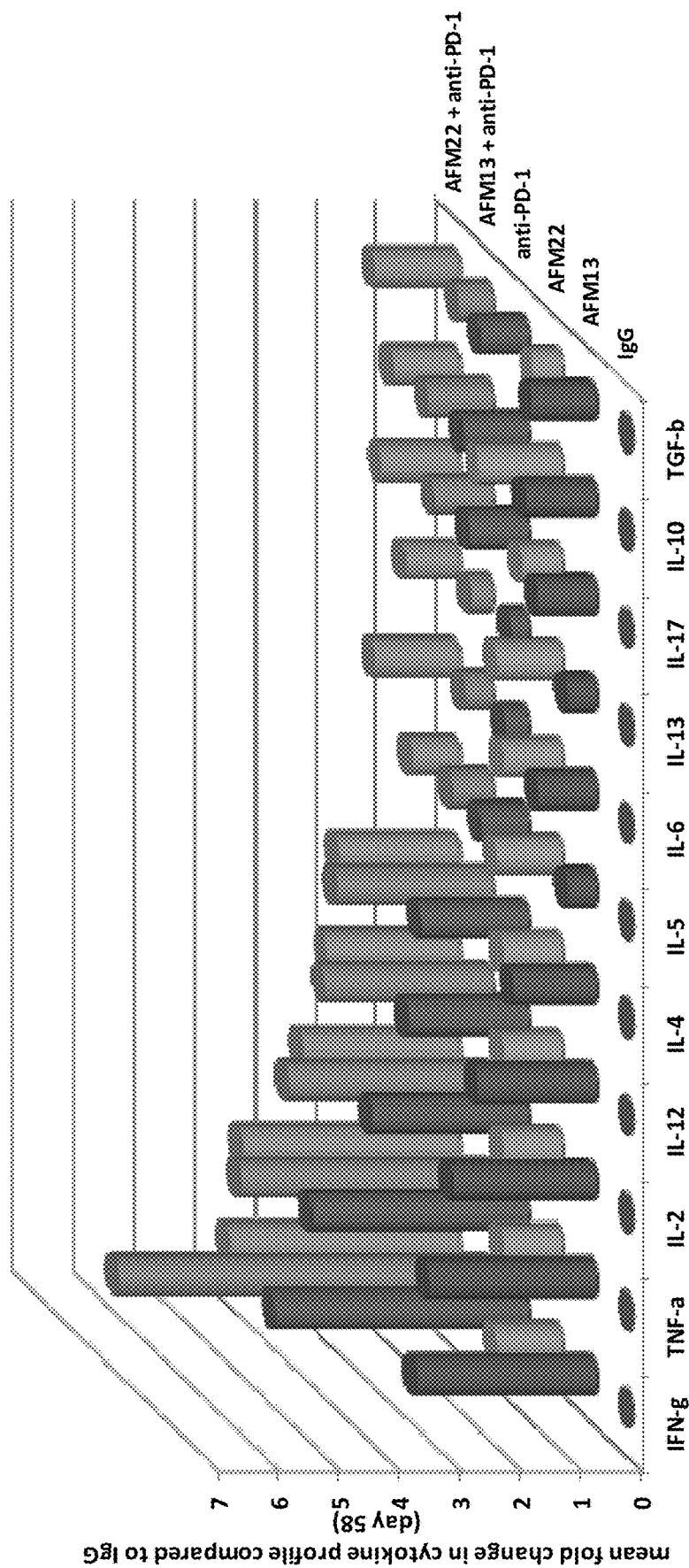
FIG. 9 shows intratumoral cytokine profile of four in vivo PDX models at day 58
Figure 10A:
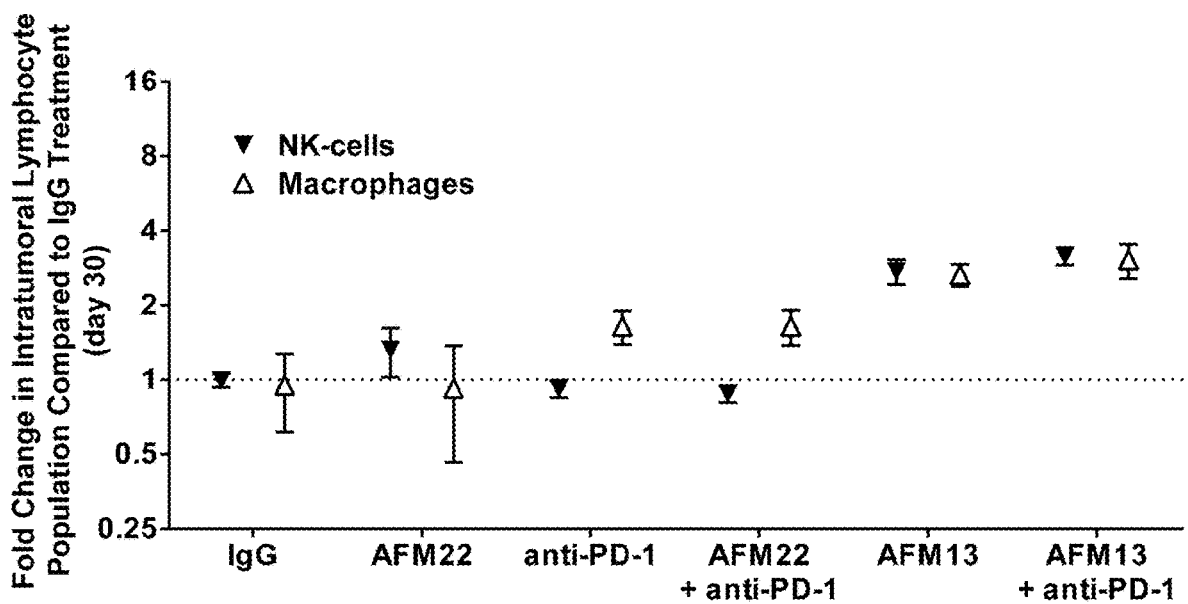
FIGS. 10A-D shows intratumoral human leukocyte profiles. $Rag2^{-/-}$ $IL2R\gamma^{null}$ mice were engrafted with tumor pieces from HL patients on day 0 and reconstituted with autologous patient-derived PBMC by i.p. injection on day 28. Antibody treatment started on day 28 with i.p. injection of 5 mg/kg AFM13 or control tandem diabody AFM22 or IgG and injection of anti-PD-1 with one day delay once a week for a total of three cycles. On day 30 (A, C) and day 58 (B, D) mice were sacrificed and tumor infiltrating $CD3^-/CD56^+$NK-cells and $CD11b^+/HLA-DR^+/CD163^+$macrophages (A, B) or $CD3^+/CD8^+$ T-cells, $CD3^+/CD4^+$ T-cells and $CD11c^+/CD80^+/CD86^+$ dendritic cells (C, D) were quantified.
Figure 10B:
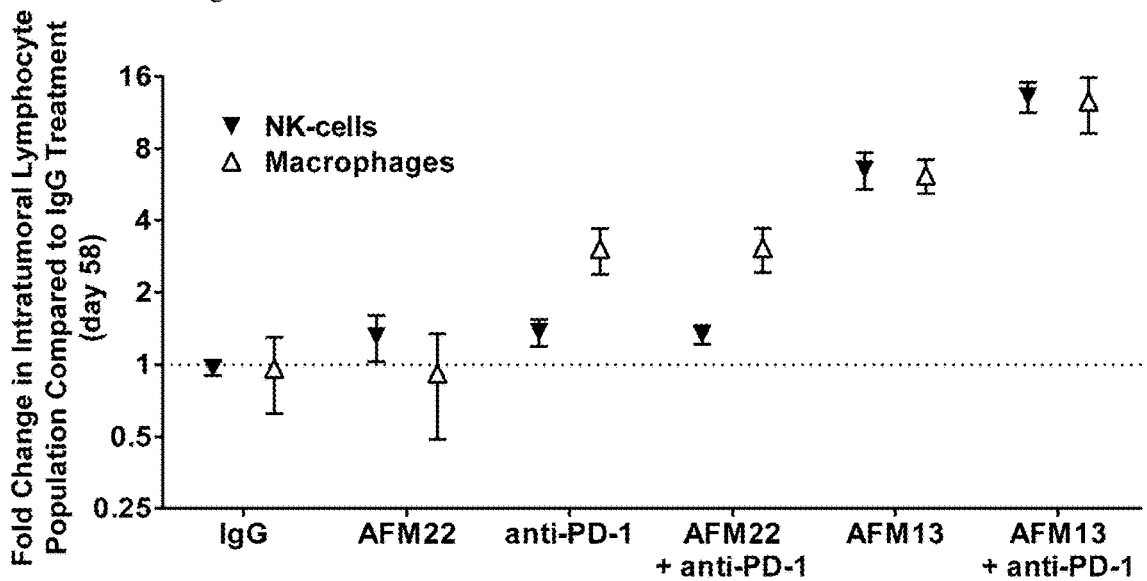
Figure 10C:
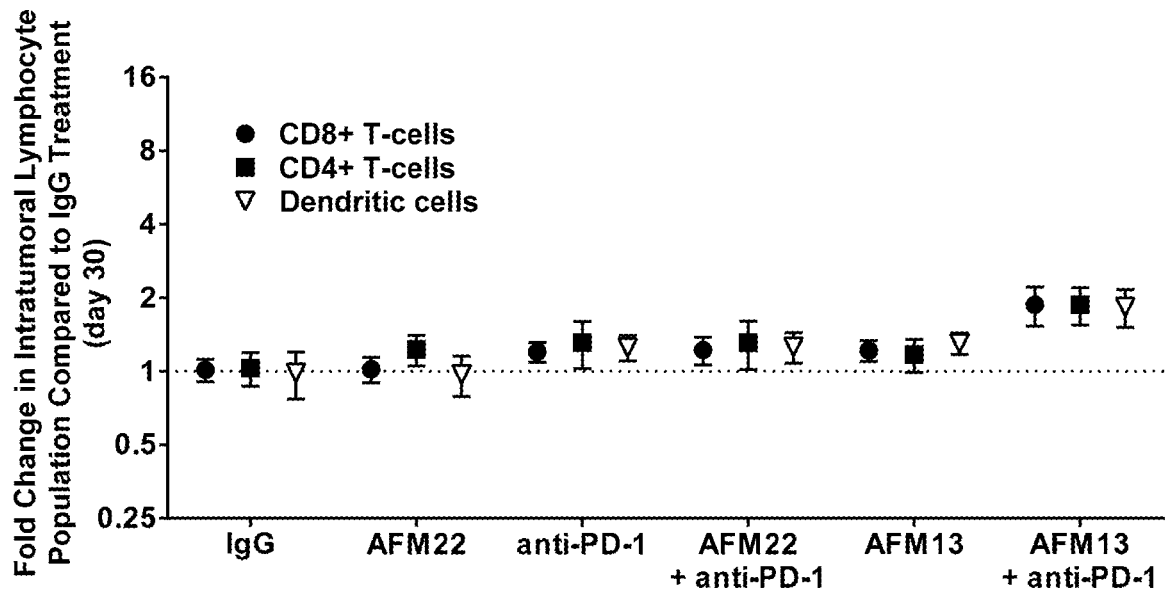
Figure 10D:
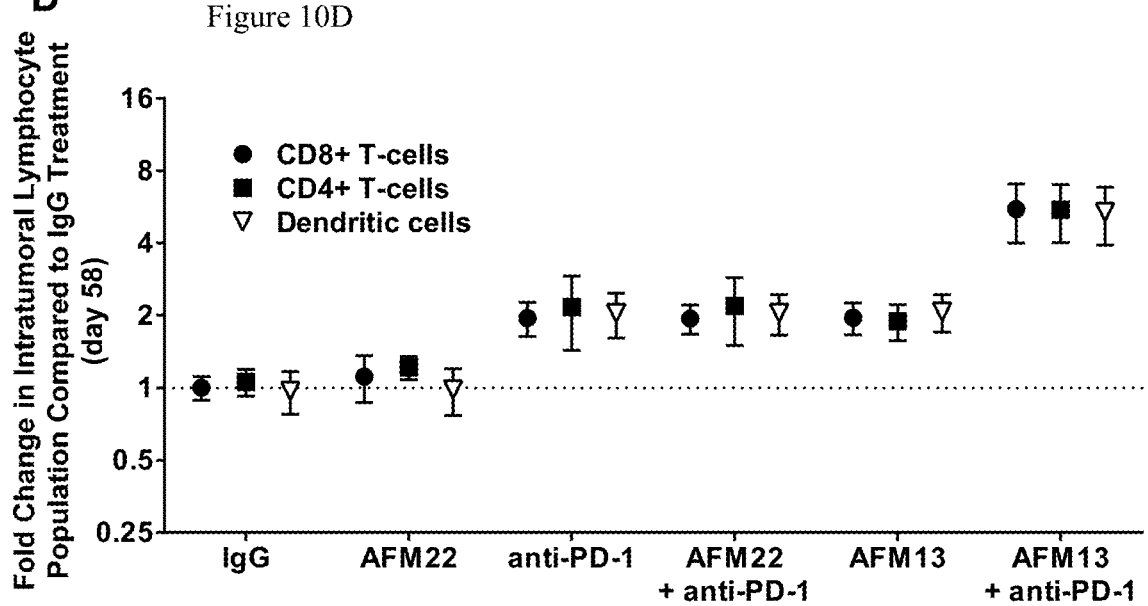

In further experiments with the same PDX model of above and anti-PD-1 (pembrolizumab) tumor size, tumor infiltrating human lymphocytes, myeloid cells and intratumoral cytokines were evaluated on days 30, 44, and 58, i.e. 2, 16 and 30 days after treatment start. Monotherapy with CD30/CD16A tandem diabody was reproducibly more potent than monotherapy with anti-PD-1 and synergy was observed when both agents were combined. Analysis of the tumors on day 58 revealed a strong correlation between tumor growth inhibition (FIG. 8A) and levels of tumor infiltrating NK-cells, T-cells, myeloid cells (FIG. 8B) and intratumoral cytokines such as IFNγ (FIG. 9). In contrast to anti-PD-1 monotherapy, which only induced T-cell infiltration, monotherapy with CD30/CD16A tandem diabody was able to induce infiltration of NK- and T-cells in the tumors, however the combination of CD30/CD16A tandem diabody with anti-PD-1 further enhanced infiltration of both, NK- and T-cells. CD30/CD16A tandem diabody resulted in stronger infiltration of macrophages than anti-PD-1, which was also increased by the combination of both agents (FIG. 8B), therefore further supporting crosstalk between innate and adaptive immunity. Furthermore, tumor analyses at the earlier time-points day 30 (FIG. 6B) and day 44 (FIG. 7B) showed that the initial immune response is characterized by NK-cell infiltration and activation, as well as infiltration of macrophages, whilst the adaptive immune response by T-cells and activated dendritic cells was more pronounced on day 58 (FIG. 8B). Combining CD30/CD16A tandem diabody and anti-PD-1 augments infiltration and activation of all immune subpopulations (FIG. 8B). As early as 2 days after treatment (day 30) CD30/CD16A tandem diabody monotherapy induced an infiltration of both NK cells and macrophages in the tumors. This effect was enhanced over time and both immune cell populations demonstrated strong tandem diabody-mediated infiltration of the tumors towards the end of the experiment (day 58). When CD30/CD16A tandem diabody was combined with the immuno-modulating antibody anti-PD-1 the effect on innate immunity was initially driven by tandem diabody alone, but the anti-PD-1 treatment did result in a more pronounced innate cell infiltration at the end of the experiment (FIG. 10).

In summary, the data shows strong antitumor efficacy when CD30/CD16A tandem diabody is combined with anti-PD-1 checkpoint blockade in Hodgkin lymphoma PDX models, mediated by tumor-infiltrating lymphocytes (CD4+ and CD8+ T-cells, macrophages and dendritic cells). Hence, the initial anti-tumor response induced by CD30/CD16A tandem diabody is driven by the recruitment and activation of innate immune cells such as NK-cells and macrophages, and their activation results in crosstalk between innate and adaptive immunity such as CD4 and CD8+ T-cells correlating with efficient tumor growth control. These observations also correlate with the release of intra-tumoral cytokines such as IFNγ or TNFα.

---

SEQUENCE SUMMARY

---

SEQ ID NO: 1
Amino acid sequence of bispecific tandem diabody
CD30/CD16A
QVQLVQSGAEVKKPGESLKVSCKASGYTFTSYYMHWVRQAPGQGLEWMGI
INPSGGSTSYAQKFQGRVTMTRDTSTSTVYMELSSLRSEDTAVYYCARGS
AYYYDFADYWGQGTLVTVSSGGSGGSGGSDIVMTQSPKFMSTSVGDRVTV
TCKASQNVGTNVAWFQQKPGQSPKVLIYSASYRYSGVPDRFTGSGSGTDF
TLTISNVQSEDLAEYFCQQYHTYPLTFGGGTKLEINGGSGGSGGSQVQLQ
QSGAELARPGASVKMSCKASGYTFTTYTIHWVRQRPGHDLEWIGYINPSS
GYSDYNQNFKGKTTLTADKSSNTAYMQLNSLTSEDSAVYYCARRADYGNY
EYTWFAYWGQGTTVTVSSGGSGGSGGSSYVLTQPSSVSVAPGQTATISCG
GHNIGSKNVHWYQQRPGQSPVLVIYQDNKRPSGIPERFSGSNSGNTATLT
ISGTQAMDEADYYCQVWDNYSVLFGGGTKLTVL SEQ ID NO: 2
Heavy chain variable domain amino acid sequence
anti-CD30
QVQLQQSGAELARPGASVKMSCKASGYTFTTYTIFIWVRQRPGHDLEWIG
YINPSSGYSDYNQNFKGKTTLTADKSSNTAYMQLNSLTSEDSAVYYCARR
ADYGNYEYTWFAYWGQGTTVTVSS SEQ ID NO: 3
Light chain variable domain amino acid sequence
anti-CD30
DIVMTQSPKFMSTSVGDRVTVTCKASQNVGTNVAWFQQKPGQSPKVLIYS
ASYRYSGVPDRFTGSGSGTDFTLTISNVQSEDLAEYFCQQYHTYPLTFGG
GTKLEIN SEQ ID NO: 4
Heavy chain variable domain amino acid sequence
anti-CD16A
QVQLVQSGAEVKKPGESLKVSCKASGYTFTSYYMHWVRQAPGQGLEWMGI
INPSGGSTSYAQKFQGRVTMTRDTSTSTVYMELSSLRSEDTAVYYCARGS
AYYYDFADYWGQGTLVTVSS SEQ ID NO: 5
Light chain variable domain amino acids sequence
anti-CD16A
SYVLTQPSSVSVAPGQTATISCGGHNIGSKNVHWYQQRPGQSPVLVIYQD
NKRPSGIPERFSGSNSGNTATLTISGTQAMDEADYYCQVWDNYSVLFGGG
TKLTVL

---

The invention is further described by the following numbered paragraphs:

1. A combination of (i) a multifunctional antibody having specificity for CD30 and CD16A and (ii) an anti-PD-1 antibody, for use in a method of treating a tumor.

2. The combination of paragraph 1, wherein the combination is used in a method for increasing the innate immune response as compared with that of the multifunctional antibody having specificity for CD30 and CD16A alone.

3. The combination of paragraph 2, wherein the increased innate immune response is an increased intratumoral cell infiltration of innate cells into the tumor.

4. The combination of paragraph 3, wherein intratumoral infiltration of macrophages, dendritic cells and NK-cells is increased.

5. The combination of paragraph 4, wherein further the intratumoral infiltration of CD4+ and CD8+ T-cells is increased.

6. The combination of any one of paragraphs 1 to 5, wherein the tumor is a Hodgkin lymphoma.

7. The combination of any one of paragraphs 1 to 6, wherein the multifunctional antibody comprises an anti-CD30 binding domain and said anti-CD30 binding domain comprises CDR1, CDR2 and CDR3 of the heavy chain variable domain set forth in SEQ ID NO:2 and CDR1, CDR2 and CDR3 of the light chain variable domain set forth in SEQ ID NO:3.

8. The combination of paragraph 7, wherein the multifunctional antibody comprises an anti-CD30 binding domain and said anti-CD30 binding domain comprises the heavy chain variable domain set forth in SEQ ID NO:2 and the light chain variable domain set forth in SEQ ID NO:3

9. The combination of any one of paragraphs 1 to 8, wherein the multifunctional antibody comprises an anti-CD16A binding domain and said anti-CD16A binding domain comprises CDR1, CDR2 and CDR3 of the heavy chain variable domain set forth in SEQ ID NO:4 and CDR1, CDR2 and CDR3 of the light chain variable domain set forth in SEQ ID NO:5.

10. The combination of paragraph 9, wherein the multifunctional antibody comprises an anti-CD16A binding domain and said anti-CD16A binding domain comprises a heavy chain variable domain set forth in SEQ ID NO:4 and a light chain variable domain set forth in SEQ ID NO:5

11. The combination of any one of paragraphs 1 to 10, wherein the multifunctional antibody is a bispecific CD30/CD16A tandem diabody.

12. The combination of paragraph 11, wherein the bispecific CD30/CD16A tandem diabody has an amino acid sequence as set forth in SEQ ID NO:1.

13. The combination of any one of paragraphs 1-12, comprising a further agent modulating an immune checkpoint molecule selected from the group of antibodies consisting of anti-CD137 antibody and anti-CTLA-4 antibody.

14. The combination of paragraph 13, comprising the multifunctional antibody having specificity for CD30 and CD16A, anti-CD137 antibody and anti-PD-1 antibody.

15. The combination of any one of paragraphs 1-14, wherein the multifunctional antibody is administered prior to the anti-PD-1 antibody.

101. A combination of (i) a multifunctional antibody having specificity for CD30 and CD16A and (ii) an anti-PD-1 antibody, for use in a method of treating a CD30+ tumor.

102. The combination of paragraph 101, wherein the combination is used in a method for increasing the innate immune response as compared with that of the multifunctional antibody having specificity for CD30 and CD16A alone.

103. The combination of paragraph 102, wherein the increased innate immune response is an increased intratumoral cell infiltration of innate cells into the tumor.

104. The combination of paragraph 103, wherein intratumoral infiltration of macrophages, dendritic cells and NK-cells is increased.

105. The combination of paragraph 104, wherein further the intratumoral infiltration of CD4+ and CD8+ T-cells is increased.

106. The combination of any one of paragraphs 101 to 105, wherein the tumor is a Hodgkin lymphoma.

107. The combination of any one of paragraphs 101 to 106, wherein the multifunctional antibody comprises an anti-CD30 binding domain and said anti-CD30 binding domain comprises CDR1, CDR2 and CDR3 of the heavy chain variable domain set forth in SEQ ID NO:2 and CDR1, CDR2 and CDR3 of the light chain variable domain set forth in SEQ ID NO:3.

108. The combination of claim 107, wherein the multifunctional antibody comprises an anti-CD30 binding domain and said anti-CD30 binding domain comprises the heavy chain variable domain set forth in SEQ ID NO:2 and the light chain variable domain set forth in SEQ ID NO:3.

109. The combination of any one of paragraphs 101 to 108, wherein the multifunctional antibody comprises an anti-CD16A binding domain and said anti-CD16A binding domain comprises CDR1, CDR2 and CDR3 of the heavy chain variable domain set forth in SEQ ID NO:4 and CDR1, CDR2 and CDR3 of the light chain variable domain set forth in SEQ ID NO:5.

110. The combination of paragraph 109, wherein the multifunctional antibody comprises an anti-CD16A binding domain and said anti-CD16A binding domain comprises a heavy chain variable domain set forth in SEQ ID NO:4 and a light chain variable domain set forth in SEQ ID NO:5.

111. The combination of any one of paragraphss 101 to 110, wherein the multifunctional antibody is a bispecific CD30/CD16A tandem diabody.

112. The combination of paragraph 111, wherein the bispecific CD30/CD16A tandem diabody has an amino acid sequence as set forth in SEQ ID NO:1.

113. The combination of any one of paragraphs 101-112, comprising a further agent modulating an immune checkpoint molecule selected from the group of antibodies consisting of anti-CD137 antibody and anti-CTLA-4 antibody.

114. The combination of paragraph 113, comprising the multifunctional antibody having specificity for CD30 and CD16A, anti-CD137 antibody and anti-PD-1 antibody.

115. The combination of any one of paragraphs 101-114, wherein the multifunctional antibody is administered prior to the anti-PD-1 antibody.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method of treating a CD30+ tumor in a patient in need thereof comprising administering a combination of (i) a multifunctional antibody having specificity for CD30 and CD16A and (ii) an antagonistic anti-PD-1 antibody to the patient, wherein the antibody having specificity for CD30 and CD16A comprises an anti-CD30 binding domain comprising CDR1, CDR2 and CDR3 of the heavy chain variable domain set forth in SEQ ID NO:2 and CDR1, CDR2 and CDR3 of the light chain variable domain set forth in SEQ ID NO:3; and an anti-CD16A binding domain comprising CDR1, CDR2 and CDR3 of the heavy chain variable domain set forth in SEQ ID NO:4 and CDR1, CDR2 and CDR3 of the light chain variable domain set forth in SEQ ID NO:5.

2. The method of claim 1, wherein the innate immune response is increased as compared with that of the multifunctional antibody having specificity for CD30 and CD16A alone.

3. The method of claim 2, wherein the increased innate immune response is an increased intratumoral cell infiltration of innate cells into the tumor.

4. The method of claim 3, wherein intratumoral infiltration of macrophages, dendritic cells and NK-cells is increased.

5. The method of claim 4, wherein further the intratumoral infiltration of CD4+ and CD8+ T-cells is increased.

6. The method of claim 1, wherein the tumor is a Hodgkin lymphoma.

7. The method of claim 1, wherein the multifunctional antibody having specificity for CD30 and CD16A comprises an anti-CD30 binding domain and said anti-CD30 binding domain comprises the heavy chain variable domain set forth in SEQ ID NO:2 and the light chain variable domain set forth in SEQ ID NO:3; and an anti-CD16A binding domain comprising the heavy chain variable domain set forth in SEQ ID NO:4 and the light chain variable domain set forth in SEQ ID NO:5.

8. The method of claim 1, wherein the multifunctional antibody is a bispecific CD30/CD16A tandem diabody.

9. The method of claim 8, wherein the bispecific CD30/CD16A tandem diabody has an amino acid sequence as set forth in SEQ ID NO:1.

10. The method of claim 1, comprising a further agent modulating an immune checkpoint molecule selected from the group of antibodies consisting of anti-CD137 antibody and anti-CTLA-4 antibody.

11. The method of claim 10, comprising the multifunctional antibody having specificity for CD30 and CD16A, anti-CD137 antibody and anti-PD-1 antibody.

12. The method of claim 1, wherein the multifunctional antibody is administered prior to the anti-PD-1 antibody.

13. The method of claim 1, wherein the antagonistic anti-PD-1 antibody is selected from the group consisting of pembrolizumab and nivolumab.

14. The method of claim 13, wherein the antagonistic anti-PD-1 antibody is pembrolizumab.

15. The method of claim 1, wherein the multifunctional antibody having specificity for CD30 and CD16A is bispecific.

16. A method of treating a CD30+ tumor in a patient in need thereof comprising administering a combination of
(i) a bispecific antibody having specificity for CD30 and CD16A and
(ii) pembrolizumab to the patient,
wherein the bispecific antibody having specificity for CD30 and CD16A
is a bispecific CD30/CD16A tandem diabody, and
comprises an anti-CD30 binding domain comprising CDR1, CDR2 and CDR3 of the heavy chain variable domain set forth in SEQ ID NO:2 and CDR1, CDR2 and CDR3 of the light chain variable domain set forth in SEQ ID NO:3, and an anti-CD16A binding domain comprising CDR1, CDR2 and CDR3 of the heavy chain variable domain set forth in SEQ ID NO:4 and CDR1, CDR2 and CDR3 of the light chain variable domain set forth in SEQ ID NO:5.

17. The method of claim 16, wherein the bispecific CD30/CD16A tandem diabody has an amino acid sequence as set forth in SEQ ID NO:1.

* * * * *